US008388680B2

(12) United States Patent  
Starksen et al.

(10) Patent No.: US 8,388,680 B2
(45) Date of Patent: Mar. 5, 2013

(54) METHODS AND DEVICES FOR CATHETER ADVANCEMENT AND DELIVERY OF SUBSTANCES THERETHROUGH

(75) Inventors: Niel F. Starksen, Los Altos Hills, CA (US); Karl S. Im, Palo Alto, CA (US); Mariel Fabro, San Jose, CA (US); Stephen C. Meier, Santa Clara, CA (US); Anne T. Meier, legal representative, Santa Clara, CA (US); Eugene Serina, Union City, CA (US)

(73) Assignee: Guided Delivery Systems, Inc., Santa Clara, CA (US)

( * ) Notice: Subject to any disclaimer, the term of this patent is extended or adjusted under 35 U.S.C. 154(b) by 680 days.

(21) Appl. No.: 11/583,627

(22) Filed: Oct. 18, 2006

(65) Prior Publication Data

US 2008/0172035 A1    Jul. 17, 2008

(51) Int. Cl.  
*A61F 2/24* (2006.01)  
*A61M 31/00* (2006.01)

(52) U.S. Cl. .............. 623/2.11; 604/508; 604/510
(58) Field of Classification Search .......... 604/508, 604/510; 606/139, 151, 219, 143, 144, 148; 623/2.1, 2.11, 2.14, 2.17, 2.18, 2.38, 2.4, 623/2.22, 3.3; 600/16–18
See application file for complete search history.

(56) References Cited

U.S. PATENT DOCUMENTS

| 3,656,185 A | 4/1972 | Carpentier |
| 3,773,034 A | 11/1973 | Burns et al. |
| 3,961,419 A | 6/1976 | Schwartz |
| 3,976,079 A | 8/1976 | Samuels et al. |
| 4,034,473 A | 7/1977 | May |
| 4,042,979 A | 8/1977 | Angell |
| 4,053,979 A | 10/1977 | Tuthill et al. |
| 4,069,825 A | 1/1978 | Akiyama |
| 4,273,127 A | 6/1981 | Auth et al. |

(Continued)

FOREIGN PATENT DOCUMENTS

| JP | 2003-500121 A | 1/2003 |
| WO | WO-95/15715 A1 | 6/1995 |

(Continued)

OTHER PUBLICATIONS

International Search Report mailed on May 6, 2008 for PCT Application PCT/US07/22122 filed on Oct. 16, 2007, 2 pages.

(Continued)

*Primary Examiner* — Nicholas Lucchesi  
*Assistant Examiner* — Pritesh Patel  
(74) *Attorney, Agent, or Firm* — Morrison & Foerster LLP

(57) ABSTRACT

Methods and devices for successively advancing a plurality of catheters over a guide element to a body tissue are described. In some of the methods, the guide element may be attached to the body tissue, which may be accessible minimally invasively. In certain variations, the guide element may not be detached from the body tissue after the catheters have been advanced over the guide element. The methods may further comprise deploying at least one implant from at least one of the plurality of catheters. In some variations, a method may comprise advancing a first delivery catheter to a first region of a body tissue, deploying a first anchor from the first delivery catheter, where the first anchor is attached to a guide element, proximally withdrawing the first delivery catheter, advancing a second delivery catheter over the guide element, and deploying a second anchor from the second delivery catheter.

57 Claims, 22 Drawing Sheets

U.S. PATENT DOCUMENTS

| | | |
|---|---|---|
| 4,290,151 A | 9/1981 | Massana |
| 4,384,406 A | 5/1983 | Tischlinger |
| 4,445,509 A | 5/1984 | Auth |
| 4,489,446 A | 12/1984 | Reed |
| 4,494,542 A | 1/1985 | Lee |
| 4,726,371 A | 2/1988 | Gibbens |
| 4,758,221 A | 7/1988 | Jureidini |
| 4,845,851 A | 7/1989 | Warthen |
| 4,848,341 A | 7/1989 | Ahmad |
| 4,850,354 A | 7/1989 | McGurk-Burleson et al. |
| 4,969,893 A | 11/1990 | Swor |
| 5,053,047 A | 10/1991 | Yoon |
| 5,064,431 A | 11/1991 | Gilbertson et al. |
| 5,084,058 A | 1/1992 | Li |
| 5,133,723 A | 7/1992 | Li et al. |
| 5,195,990 A | 3/1993 | Weldon |
| 5,221,255 A | 6/1993 | Mahurkar et al. |
| 5,314,407 A | 5/1994 | Auth et al. |
| 5,324,298 A | 6/1994 | Phillips et al. |
| 5,346,500 A | 9/1994 | Suchart |
| 5,358,479 A | 10/1994 | Wilson |
| 5,364,407 A | 11/1994 | Poll |
| 5,368,564 A | 11/1994 | Savage |
| 5,383,905 A | 1/1995 | Golds et al. |
| 5,417,700 A | 5/1995 | Egan |
| 5,423,837 A | 6/1995 | Mericle et al. |
| 5,437,680 A | 8/1995 | Yoon |
| 5,439,470 A | 8/1995 | Li |
| 5,452,513 A | 9/1995 | Zinnbauer et al. |
| 5,474,572 A | 12/1995 | Hayhurst |
| 5,507,725 A | 4/1996 | Savage et al. |
| 5,527,323 A | 6/1996 | Jervis et al. |
| 5,545,168 A | 8/1996 | Burke |
| 5,565,122 A | 10/1996 | Zinnbauer et al. |
| 5,571,215 A | 11/1996 | Sterman et al. |
| 5,626,614 A | 5/1997 | Hart |
| 5,630,824 A | 5/1997 | Hart |
| 5,640,955 A | 6/1997 | Ockuly et al. |
| 5,669,917 A | 9/1997 | Sauer et al. |
| 5,690,655 A | 11/1997 | Hart et al. |
| 5,718,725 A | 2/1998 | Sterman et al. |
| 5,735,290 A | 4/1998 | Sterman et al. |
| 5,741,260 A | 4/1998 | Songer et al. |
| 5,741,301 A | 4/1998 | Pagedas |
| 5,752,964 A | 5/1998 | Mericle |
| 5,755,730 A | 5/1998 | Swain et al. |
| 5,810,848 A | 9/1998 | Hayhurst |
| 5,810,853 A | 9/1998 | Yoon |
| 5,817,107 A | 10/1998 | Schaller |
| 5,860,993 A | 1/1999 | Thompson et al. |
| 5,868,733 A | 2/1999 | Ockuly et al. |
| 5,879,371 A | 3/1999 | Gardiner et al. |
| 5,902,321 A | 5/1999 | Caspari et al. |
| 5,904,657 A * | 5/1999 | Unsworth et al. ............ 600/585 |
| 5,906,579 A | 5/1999 | Vander Salm et al. |
| 5,916,147 A | 6/1999 | Boury |
| 5,919,208 A | 7/1999 | Valenti |
| 5,961,440 A | 10/1999 | Schweich, Jr. et al. |
| 6,015,428 A | 1/2000 | Pagedas |
| 6,050,936 A | 4/2000 | Schweich, Jr. et al. |
| 6,056,743 A | 5/2000 | Ellis et al. |
| 6,059,715 A | 5/2000 | Schweich, Jr. et al. |
| 6,066,160 A | 5/2000 | Colvin et al. |
| 6,125,852 A | 10/2000 | Stevens et al. |
| 6,162,168 A | 12/2000 | Schweich, Jr. et al. |
| 6,183,469 B1 | 2/2001 | Thapliyal et al. |
| 6,203,531 B1 | 3/2001 | Ockuly et al. |
| 6,228,096 B1 | 5/2001 | Marchand |
| 6,254,620 B1 | 7/2001 | Koh et al. |
| 6,258,118 B1 | 7/2001 | Baum et al. |
| 6,260,552 B1 | 7/2001 | Mortier et al. |
| 6,378,289 B1 | 4/2002 | Trudeau et al. |
| 6,406,420 B1 | 6/2002 | McCarthy et al. |
| 6,432,123 B2 | 8/2002 | Schwartz et al. |
| 6,491,689 B1 | 12/2002 | Ellis et al. |
| 6,540,755 B2 | 4/2003 | Ockuly et al. |
| 6,589,160 B2 | 7/2003 | Schweich, Jr. et al. |
| 6,629,534 B1 | 10/2003 | St. Goar et al. |
| 6,648,903 B1 | 11/2003 | Pierson, III |
| 6,669,687 B1 | 12/2003 | Saadat |
| 6,699,263 B2 | 3/2004 | Cope |
| 6,716,243 B1 | 4/2004 | Colvin et al. |
| 6,723,038 B1 | 4/2004 | Schroeder et al. |
| 6,733,509 B2 | 5/2004 | Nobles et al. |
| 6,746,471 B2 | 6/2004 | Mortier et al. |
| 6,793,618 B2 | 9/2004 | Schweich, Jr. et al. |
| 6,818,001 B2 | 11/2004 | Wulfman et al. |
| 6,849,077 B2 | 2/2005 | Ricci |
| 6,908,424 B2 | 6/2005 | Mortier et al. |
| 6,951,557 B2 | 10/2005 | Ellis et al. |
| 6,976,995 B2 | 12/2005 | Mathis et al. |
| 6,986,775 B2 | 1/2006 | Morales et al. |
| 6,997,931 B2 | 2/2006 | Sauer et al. |
| 7,037,334 B1 | 5/2006 | Hlavka et al. |
| 7,048,754 B2 | 5/2006 | Martin et al. |
| 7,101,395 B2 | 9/2006 | Tremulis et al. |
| 7,125,421 B2 | 10/2006 | Termulis et al. |
| 7,166,127 B2 | 1/2007 | Spence et al. |
| 7,186,262 B2 | 3/2007 | Saadat |
| 7,189,199 B2 | 3/2007 | McCarthy et al. |
| 7,214,230 B2 | 5/2007 | Brock et al. |
| 7,235,086 B2 | 6/2007 | Sauer et al. |
| 7,241,310 B2 | 7/2007 | Taylor et al. |
| 7,257,450 B2 | 8/2007 | Auth et al. |
| 7,326,231 B2 | 2/2008 | Phillips et al. |
| 7,331,972 B1 | 2/2008 | Cox |
| 7,452,325 B2 | 11/2008 | Schaller |
| 7,618,449 B2 | 11/2009 | Termulis et al. |
| 7,632,308 B2 | 12/2009 | Loulmet |
| 7,722,523 B2 | 5/2010 | Mortier et al. |
| 7,740,638 B2 | 6/2010 | Hyde |
| 7,776,812 B2 | 8/2010 | Lang et al. |
| 7,832,406 B2 | 11/2010 | Ellis et al. |
| 2001/0031979 A1 | 10/2001 | Ricci |
| 2001/0047165 A1 | 11/2001 | Makower et al. |
| 2002/0007190 A1 | 1/2002 | Wulfman et al. |
| 2002/0035393 A1* | 3/2002 | Lashinski et al. ............ 623/1.11 |
| 2002/0065536 A1 | 5/2002 | Hart et al. |
| 2002/0077524 A1 | 6/2002 | Schweich, Jr. et al. |
| 2002/0087169 A1 | 7/2002 | Brock et al. |
| 2002/0133092 A1* | 9/2002 | Oslund et al. ................. 600/585 |
| 2002/0183835 A1 | 12/2002 | Taylor et al. |
| 2002/0198536 A1 | 12/2002 | Trout, III et al. |
| 2003/0009196 A1 | 1/2003 | Peterson |
| 2003/0032979 A1 | 2/2003 | Mortier et al. |
| 2003/0045893 A1 | 3/2003 | Ginn |
| 2003/0060813 A1 | 3/2003 | Loeb et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0158581 A1 | 8/2003 | Levinson |
| 2003/0233105 A1 | 12/2003 | Gayton |
| 2004/0019378 A1 | 1/2004 | Hlavka et al. |
| 2004/0092962 A1 | 5/2004 | Thornton et al. |
| 2004/0118415 A1* | 6/2004 | Hall et al. ..................... 128/898 |
| 2004/0122450 A1 | 6/2004 | Oren et al. |
| 2004/0148020 A1* | 7/2004 | Vidlund et al. .............. 623/2.36 |
| 2004/0152947 A1 | 8/2004 | Schroeder et al. |
| 2004/0172046 A1 | 9/2004 | Hlavka et al. |
| 2004/0181238 A1 | 9/2004 | Zarbatany et al. |
| 2004/0186486 A1 | 9/2004 | Roue et al. |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0236372 A1 | 11/2004 | Anspach, III et al. |
| 2004/0243227 A1 | 12/2004 | Starksen et al. |
| 2005/0055087 A1 | 3/2005 | Starksen |
| 2005/0065550 A1 | 3/2005 | Starksen et al. |
| 2005/0075723 A1 | 4/2005 | Schroeder et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0119673 A1 | 6/2005 | Gordon et al. |
| 2005/0119735 A1 | 6/2005 | Spence et al. |
| 2005/0137689 A1 | 6/2005 | Salahieh et al. |
| 2005/0184122 A1 | 8/2005 | Hlavka et al. |
| 2005/0192629 A1 | 9/2005 | Saadat et al. |

| | | |
|---|---|---|
| 2005/0197694 A1 | 9/2005 | Pai et al. |
| 2005/0209690 A1 | 9/2005 | Mathis et al. |
| 2005/0273138 A1 | 12/2005 | To et al. |
| 2006/0025750 A1 | 2/2006 | Starksen et al. |
| 2006/0025784 A1 | 2/2006 | Starksen et al. |
| 2006/0058817 A1 | 3/2006 | Starksen et al. |
| 2006/0069429 A1 | 3/2006 | Spence et al. |
| 2006/0122633 A1 | 6/2006 | To et al. |
| 2006/0129188 A1 | 6/2006 | Starksen et al. |
| 2006/0155363 A1 | 7/2006 | LaDuca et al. |
| 2006/0161040 A1 | 7/2006 | McCarthy et al. |
| 2006/0178682 A1 | 8/2006 | Boehlke |
| 2006/0184203 A1 | 8/2006 | Martin et al. |
| 2006/0190030 A1* | 8/2006 | To et al. .................. 606/205 |
| 2006/0229708 A1 | 10/2006 | Powell et al. |
| 2006/0241340 A1 | 10/2006 | Schroeder et al. |
| 2006/0264975 A1 | 11/2006 | Pipenhagen et al. |
| 2006/0270976 A1 | 11/2006 | Savage et al. |
| 2006/0271101 A1 | 11/2006 | Saadat et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010852 A1 | 1/2007 | Blaeser et al. |
| 2007/0010857 A1 | 1/2007 | Sugimoto et al. |
| 2007/0016250 A1 | 1/2007 | Blaeser et al. |
| 2007/0016287 A1 | 1/2007 | Cartledge et al. |
| 2007/0032820 A1 | 2/2007 | Chin-Chen et al. |
| 2007/0038293 A1 | 2/2007 | St. Goar et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0066994 A1 | 3/2007 | Blaeser et al. |
| 2007/0093805 A1 | 4/2007 | Auth et al. |
| 2007/0100356 A1 | 5/2007 | Lucatero et al. |
| 2007/0112422 A1 | 5/2007 | Dehdashtian |
| 2007/0112424 A1 | 5/2007 | Spence et al. |
| 2008/0051703 A1 | 2/2008 | Thornton et al. |
| 2008/0058765 A1 | 3/2008 | Jais et al. |
| 2008/0065156 A1 | 3/2008 | Hauser et al. |
| 2008/0097489 A1 | 4/2008 | Goldfarb et al. |
| 2008/0103439 A1 | 5/2008 | Torrance et al. |
| 2008/0119882 A1 | 5/2008 | Cox |
| 2008/0294177 A1 | 11/2008 | To et al. |
| 2009/0182417 A1 | 7/2009 | Tremulis et al. |
| 2009/0222083 A1 | 9/2009 | Nguyen et al. |
| 2009/0276038 A1 | 11/2009 | Tremulis et al. |
| 2010/0076408 A1 | 3/2010 | Krever et al. |
| 2010/0076548 A1 | 3/2010 | Konno |
| 2010/0094213 A1 | 4/2010 | Horn et al. |
| 2010/0094314 A1 | 4/2010 | Hernlund et al. |
| 2010/0121349 A1 | 5/2010 | Meier et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |

FOREIGN PATENT DOCUMENTS

| | | |
|---|---|---|
| WO | WO-96/39942 A1 | 12/1996 |
| WO | WO-97/27799 A1 | 8/1997 |
| WO | WO-97/27807 A1 | 8/1997 |
| WO | WO-98/46142 A1 | 10/1998 |
| WO | WO-00/71195 A1 | 11/2000 |
| WO | WO-01/54618 A1 | 8/2001 |
| WO | WO-02/085251 A1 | 10/2002 |
| WO | WO-02/085252 A1 | 10/2002 |
| WO | WO-03/088875 A1 | 10/2003 |
| WO | WO-03/105667 A2 | 12/2003 |
| WO | WO-03/105667 A3 | 12/2003 |
| WO | WO-2004/037317 A2 | 5/2004 |
| WO | WO-2004/037317 A3 | 5/2004 |
| WO | WO-2004/082523 A2 | 9/2004 |
| WO | WO-2004/082523 A3 | 9/2004 |
| WO | WO-2004/082538 A2 | 9/2004 |
| WO | WO-2004/082538 A3 | 9/2004 |
| WO | WO-2005/062931 A2 | 7/2005 |
| WO | WO-2005/062931 A3 | 7/2005 |
| WO | WO-2005/102181 A1 | 11/2005 |
| WO | WO-2006/034243 A2 | 3/2006 |
| WO | WO-2006/034243 A3 | 3/2006 |
| WO | WO-2006/037073 A2 | 4/2006 |
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2006/116558 C2 | 11/2006 |
| WO | WO-2007/005495 A1 | 1/2007 |
| WO | WO-2007/100409 A2 | 9/2007 |
| WO | WO-2008/028135 A2 | 3/2008 |
| WO | WO-2008/028135 A3 | 3/2008 |
| WO | WO-2008/042987 A2 | 4/2008 |
| WO | WO-2008/042987 A3 | 4/2008 |
| WO | WO-2008/048626 A2 | 4/2008 |
| WO | WO-2008-048626 A3 | 4/2008 |
| WO | WO-2010/085457 A1 | 7/2010 |

OTHER PUBLICATIONS

Non-Final Office Action mailed Aug. 30, 2007, for U.S. Appl. No. 11/270,034, filed Nov. 8, 2005, ten pages.

International Preliminary Report on Patentability mailed on Apr. 30, 2008, for PCT Application PCT/US2007/022122 filed on Oct. 16, 2007, 9 pages.

Supplementary European Search Report mailed on Jun. 2, 2010, for EP Patent Application No. 07852809.8, filed on Oct. 16, 2007, 7 pages.

International Search Report mailed on Mar. 9, 2010, for PCT Patent Application No. PCT/US/2010/021440, filed on Jan. 19, 2010, 1 page.

Towne, W.D. (Jan. 1973). "Letter to the Editor: Classification of Chordae Tendineae," *Circulation* 47:209.

U.S. Appl. No. 61/160,230, filed Mar. 13, 2009, by Meier et al.

U.S. Appl. No. 61/178,910, filed May 15, 2009, by Serina et al.

Written Opinion of the International Searching Authority mailed on Mar. 9, 2010, for PCT Patent Application No. PCT/US/2010/021440, filed on Jan. 19, 2010, 5 pages.

European Search Report mailed on Dec. 6, 2011, for EP Patent Application No. 11187159.6, filed on Oct. 16, 2007, 6 pages.

Non-Final Office Action mailed on Mar. 15, 2012, for U.S. Appl. No. 12/690,109, filed Jan. 19, 2010, 7 pages.

* cited by examiner

- ADVANCE GUIDE CATHETER TO SUB-ANNULAR GROOVE —310
- ADVANCE GUIDEWIRE THROUGH LUMEN OF GUIDE CATHETER —320
- ADVANCE TUNNEL CATHETER OVER GUIDEWIRE —330
- PROXIMALLY WITHDRAW GUIDEWIRE FROM TUNNEL CATHETER —340
- ADVANCE FIRST DELIVERY CATHETER THROUGH LUMEN OF TUNNEL CATHETER —350
- DEPLOY FIRST ANCHOR FROM FIRST DELIVERY CATHETER INTO FIRST REGION OF HEART VALVE ANNULUS —360
- POSITION TUNNEL CATHETER AT DIFFERENT LOCATION —370
- ADVANCE SECOND DELIVERY CATHETER OVER TETHER, THROUGH LUMEN OF TUNNEL CATHETER —380
- DEPLOY SECOND ANCHOR FROM SECOND DELIVERY CATHETER INTO SECOND REGION OF HEART VALVE ANNULUS —390

650

652

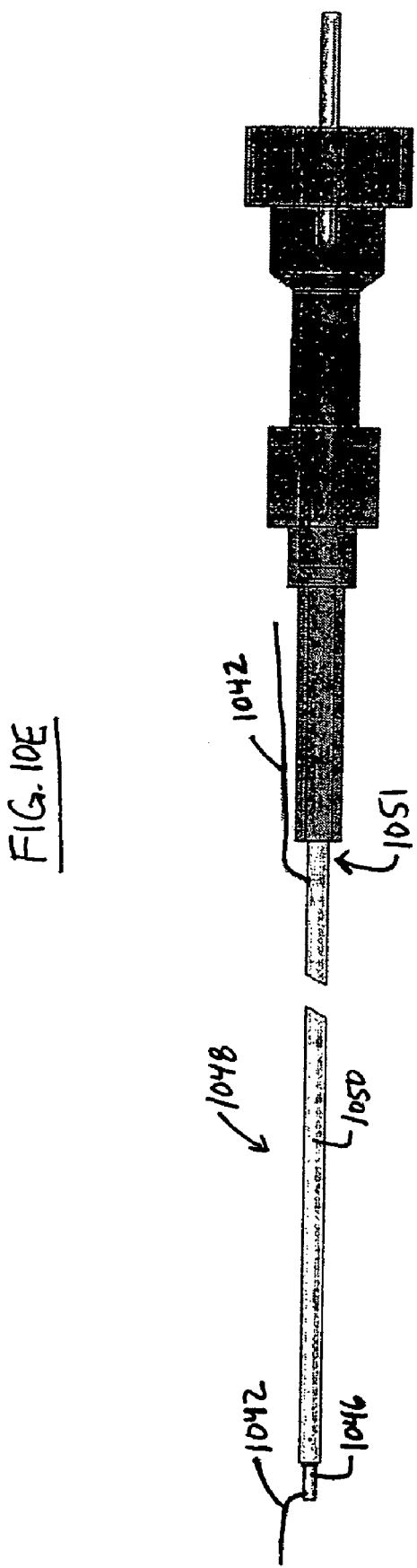

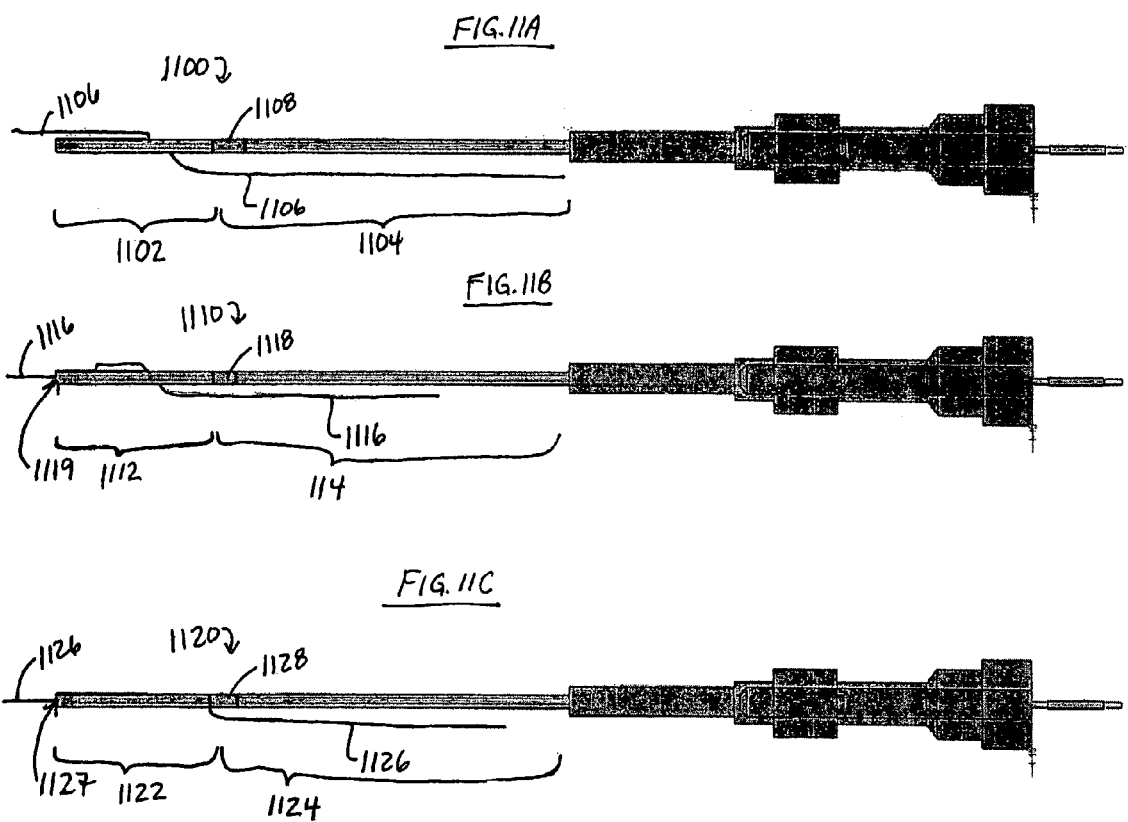

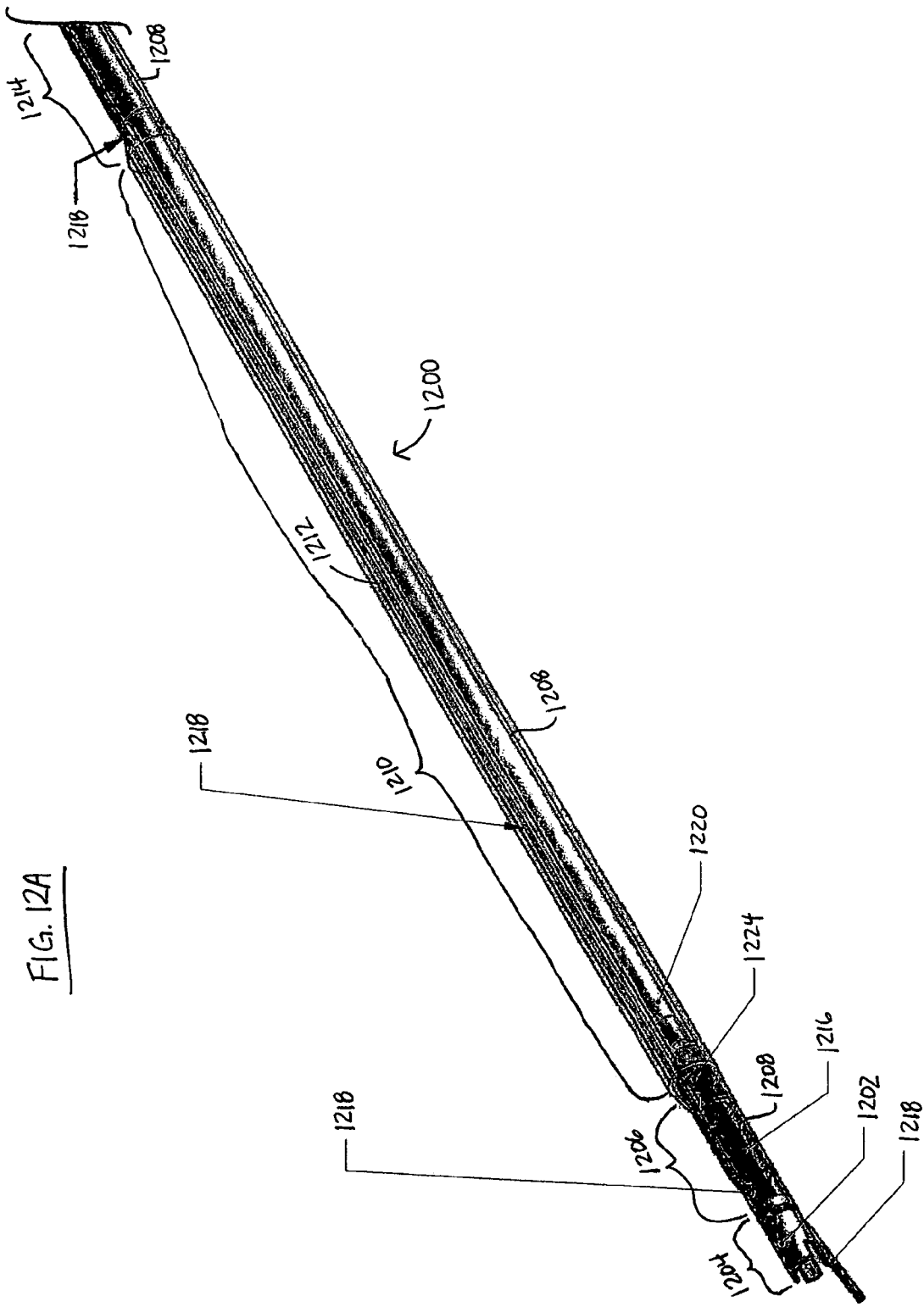

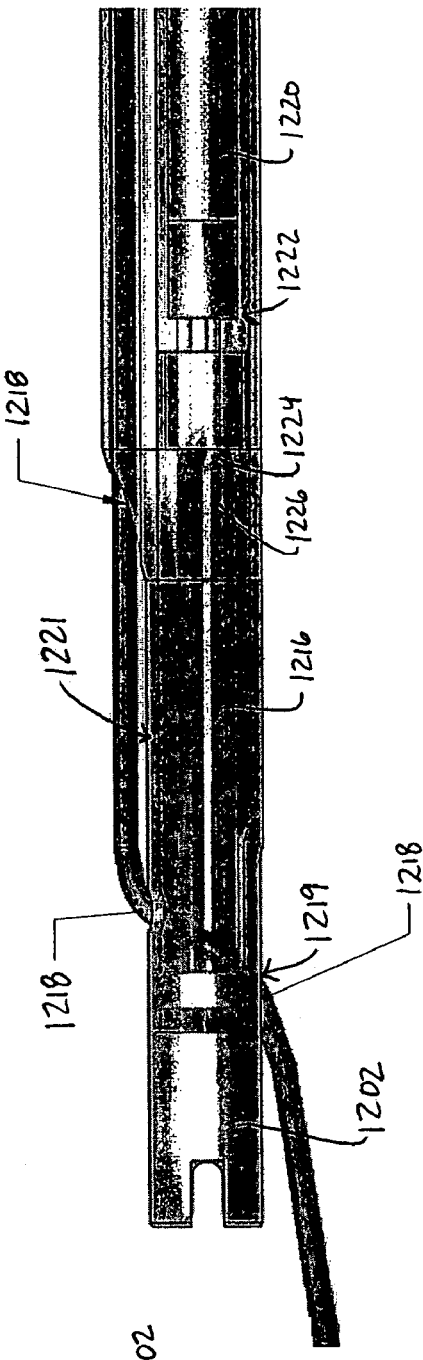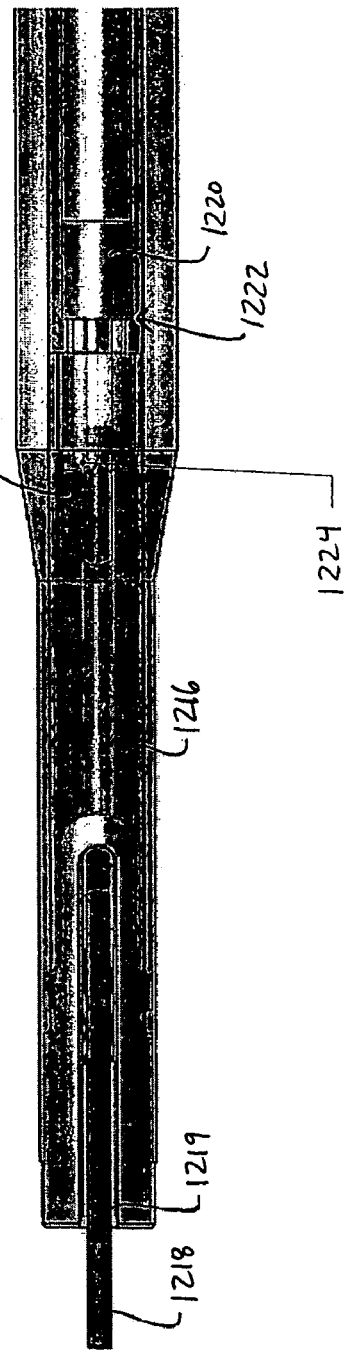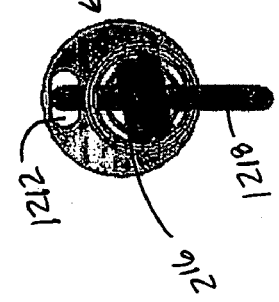

METHODS AND DEVICES FOR CATHETER ADVANCEMENT AND DELIVERY OF SUBSTANCES THERETHROUGH

TECHNICAL FIELD

The methods and devices described herein relate generally to the field of advancement of catheters over a guide element and delivery of substances through those catheters (e.g., implants, such as anchors or leads, or drugs). More specifically, the methods described here are in the field of successive advancement of a plurality of catheters over a guide element where the guide element is attached to a body tissue that is accessible minimally invasively, or where the guide element if left behind as an implant. The methods and devices described here may have particular utility in the area of mitral valve repair.

BACKGROUND

Advances have been made in the techniques and tools used in minimally invasive surgery. For example, catheters are now routinely used to access various body tissues (e.g., organs such as the heart, and vessels, such as coronary arteries). Procedures that require prolonged access to the body tissue and exchange of various tools are often lengthy due to the number of different tools that must be passed to the target site from a proximal position outside the patient's body. Methods of rapid-exchange and over-the-wire catheter systems have been developed to try to compensate for and reduce surgery times.

Rapid-exchange catheters generally include a guidewire lumen that extends for only a portion of the length of the catheter shaft. A rapid-exchange catheter may be relatively easily threaded over a guidewire, delivered to a target site, and withdrawn from the target site. Because rapid-exchange catheters do not need to be threaded over the entire length of a guidewire, rapid-exchange catheters may be relatively short in length. In some variations, a rapid-exchange catheter may be shorter in length than the guidewire over which the rapid-exchange catheter is advanced. The guidewire, in turn, may also be relatively short in length. After being withdrawn from a target site, a rapid-exchange catheter can be removed from the guidewire over which it was threaded, and exchanged with another rapid-exchange catheter, which, in turn, can be delivered to the target site over the guidewire. Some methods of removing a rapid-exchange catheter from a guidewire include withdrawing the rapid-exchange catheter over the guidewire. Other methods include using a rapid-exchange catheter with a perforated sheath, and splitting the sheath open at its perforations to remove the rapid-exchange catheter from the guidewire. The relative ease with which rapid-exchange catheters can be exchanged over a guidewire, as well as the relatively short length of rapid-exchange catheters and their guidewires, may result in reduced procedure time when such catheters are used. Additionally, rapid-exchange procedures can allow for different types of catheters (e.g., catheters having balloons of different sizes or catheters carrying different therapeutic agents) to be efficiently delivered to a target site in one-procedure. Furthermore, the use of rapid-exchange catheters in a procedure may result in a reduction in the number of operations required to complete the procedure.

Over-the-wire catheters generally include a guidewire lumen that extends along the entire length of the catheter shaft. Over-the-wire catheters may be used, for example, in peripheral procedures, such as balloon angioplasty procedures. An over-the-wire catheter may be relatively easily tracked over a guidewire and delivered to a target site. Once the over-the-wire catheter has been used to perform a procedure at the target site, it may be withdrawn over the guidewire and removed from the subject.

In instances in which multiple catheters must be delivered to a target body tissue, rapid-exchange and over-the wire techniques are particularly desirable, as they may result in reduced procedure time and/or highly accurate catheter delivery. Accordingly, additional methods and devices for advancing a plurality of catheters to a target body tissue would be desirable. Similarly, catheters configured to be advanced quickly and successively to a target body tissue would also be desirable.

BRIEF SUMMARY

Described here are methods and devices for successively advancing a plurality of catheters over a guide element to a target body tissue. Some of the methods described here generally comprise successively advancing a plurality of catheters over a guide element, wherein the guide element is attached to a body tissue. The body tissue may be accessible minimally invasively. In certain variations, the guide element may not be detached from the body tissue after the catheters have been advanced over the guide element. The methods may further comprise deploying at least one implant from at least one of the plurality of catheters. The implant may be any suitable implant. For example, it may be an anchor, a lead or electrode, or any other implant capable of fixedly securing the tether to the body tissue. In some variations, the implant is an anchor, and the anchor is configured to self-expand and self-secure into a region of the body tissue.

The body tissue may be any body tissue that is accessible minimally invasively, and in some variations, the body tissue comprises heart tissue (e.g., mitral valve tissue). In these variations, the methods may be used to deploy a series of anchors (that are carried in one or more catheters) in the region of a heart valve annulus of a subject in order to reduce mitral valve regurgitation.

Any suitable number and type of catheter may be used and advanced over the guide element. For example, the catheter may be a guide catheter, a sheath, a drug delivery catheter, a therapeutic catheter, a termination catheter, a cutting catheter, a locking catheter, a diagnostic catheter, a tool catheter, or any other suitable catheter. Some methods may include advancing one type of catheter over the guide element, and then advancing a different type of catheter over the guide element.

Other methods described here comprise advancing a first delivery catheter to a first region of a body tissue, deploying a first anchor from the first delivery catheter, wherein the first anchor is attached to a guide element, proximally withdrawing the first delivery catheter, advancing a second delivery catheter over the guide element, and deploying a second anchor from the second delivery catheter. The second anchor may be slidably coupled to the guide element, so that the guide element will not be held rigidly in place at the site of the second anchor deployment. The anchors may have eyelets through which the guide element may be slidably disposed. The guide element may be slidably coupled to the anchor with the use of a lasso prior to insertion in the delivery catheter.

The first and second anchors can be deployed to the same region or different regions of the body tissue, and any number of anchors may be deployed as desirable. In some variations, the anchors self-expand and self-secure into different regions of the body tissue. As with the methods described above, any number or type of catheters may be used, and in some variations, advancing the first delivery catheter to the first region of the body tissue comprises advancing the first delivery catheter through a tunnel catheter. The tunnel catheter may have an opening positioned along its side wall, or otherwise positioned proximally of its-distal tip, and in some variations, the first delivery catheter is advanced through the opening.

Any of the catheters described here may be pre-shaped or pre-formed in some fashion or in a particular geometry. For example, in some instances, it may be desirable for the catheter to include one or more curves to better conform to the target anatomy. In some of the variations described here, the distal portion of the tunnel catheter is pre-shaped to include at least one curve. The catheters may also have any number of suitable lumens, such as lumens that are configured to allow passage of a guide element therethrough. In some variations, a catheter described here may have a lumen that is located in either a proximal section or a distal section of the catheter, but not in both sections.

Similarly, the guide element may comprise or be made from any suitable material. For example, the guide element may be made from an artificial or natural suture material, or it may be made from a metal or shape memory alloy. The guide element may be made from one or more absorbable materials, and/or one or more non-absorbable materials. In some variations, the guide element is made from polyester impregnated with polytetrafluoroethylene. In certain variations, the guide element is a tether (e.g., a suture). In some variations, the guide element may be in the form of a wire. The guide element may be braided or woven, and/or may include multiple different layers.

Again, these methods may deploy any number of anchors, and in some variations, the anchors are deployed into heart tissue, e.g., heart tissue in the region of the mitral valve. When multiple anchors are deployed to a region of the mitral valve annulus, the guide element the delivery catheters were advanced over, may be cinched, or pulled proximally. The result may be a geometric change in at least one of the mitral valve annulus and the tissue surrounding the mitral valve annulus, a reduction in the circumference of the mitral valve annulus, enhancement of mitral valve leaflet apposition, and/or a reduction in mitral valve regurgitation.

Devices for stabilizing a catheter with respect to a body tissue are also described. In general, these devices comprise a catheter having an expandable member configured to engage against a first portion of tissue in order to stabilize the catheter with respect to a second portion of tissue. The expandable member may be any member suitable for providing such stabilization. For example, the expandable member may be a low-pressure inflatable balloon made of a compliant material, or the expandable member may be made of a shape memory material, such as a nickel titanium alloy basket or wing. In some variations, a low-pressure balloon is used and only a portion of the balloon is configured to inflate.

Catheters for advancement along a guide element are also described here. In general, the catheters comprise at least one lumen. In some variations, the catheters comprise a first and a second lumen where the first and second lumens are positioned adjacent to one another, where at least a portion of the first and second lumens are configured to allow the passage of the guide element therethrough, and where the second lumen is accessible from the first lumen. The catheter may be any suitable catheter and may have any number of desirable functions (e.g., the catheter may be a cutting catheter, a termination catheter, a device delivery catheter, a drug delivery catheter, a therapeutic catheter, a diagnostic catheter, a tool catheter, etc.). For example, the catheter may be a therapeutic catheter that is configured for use in tissue altering therapy, such as ablation. In some variations, the catheter is a device delivery catheter used for electrical pacing or for delivery of at least one anchor. In these variations, the anchor is typically positioned in the first lumen.

BRIEF DESCRIPTION OF THE DRAWINGS

FIG. 3A is a flowchart representation of a method for delivering at least two anchors into a region of a heart valve annulus.
FIGS. 10A-10E are side views of different routing configurations of guide elements in locking catheters.
FIGS. 11A-11C are side views of different routing configurations of guide elements in cutting catheters.
FIG. 12A is a perspective view of a delivery catheter,
FIG. 12B is a front view of the delivery catheter of FIG. 12A, and FIGS. 12C and 12D are side and bottom views, respectively, of a portion of the delivery catheter of FIG. 12A.

DETAILED DESCRIPTION

Figure 1:
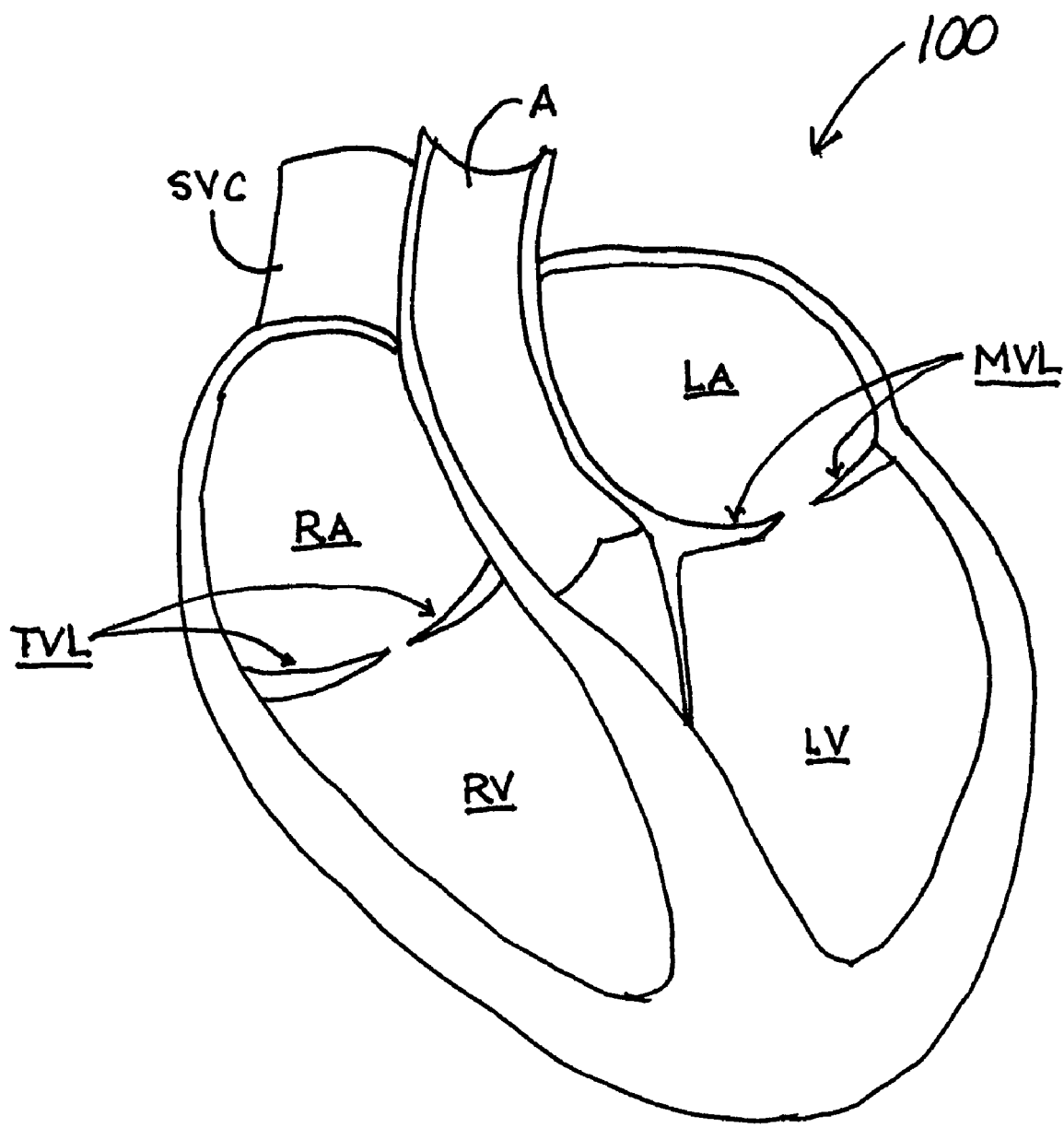
FIG. 1 is a cross-sectional view of a heart.

Described here are methods for successively advancing a plurality of catheters over a guide element, and method and devices for delivering anchors to a region of a body tissue. It should be understood from the outset that while methods of advancing a plurality of catheters to heart valve tissue are described in detail here, the methods may be used, and are contemplated for use, with any body tissue that may be accessed minimally invasively. Examples of body tissue that may be accessed minimally invasively include body tissue that may be accessed percutaneously (e.g., intravascularly), laparoscopically, endoscopically, robotically, and/or through one or more airways. Thus, the detailed description provided here of how these methods and devices are used with respect to the mitral valve heart anatomy simply represents one illustrative variation of how these methods and devices may be used. For example, the methods may be applied to the coronary sinus, the tricuspid valve, the left and/or right ventricles, and/or one or more veins. In some variations, the methods may be used with the bladder, the urethra, the lungs, the stomach, the liver, the kidneys, the gallbladder, and/or in peripheral applications (e.g., in the legs). In certain variations, the methods may be used in gastrointestinal applications or in transbrachial applications. Furthermore, the methods may be used to deliver therapy, such as tissue modification, electrical pacing, or an implant. In some variations, the guide element may be used to facilitate delivery of one or more tools to a target site. In certain variations, the guide element may be used to facilitate a robotic procedure, such as the robotic delivery of one or more tools to a target site.

In general, the methods of advancing a plurality of catheters over a guide element comprise advancing multiple catheters over a guide element, where the guide element is attached to body tissue that is accessible minimally invasively. Alternatively or additionally, the methods may comprise deploying at least one implant from one of the catheters. The implant may be any suitable or desirable implant. For example, the implant may be a lead or electrode, an anchor, or any other implant. The implant may also be of any suitable shape and size. When anchors are used, they may be configured to self-expand and self-secure into the tissue. Suitable anchors and guide elements will be described in more detail below. Similarly, any suitable catheter may be used and advanced over the guide element. For example, the catheter may be a guide catheter, a sheath, a drug delivery catheter, a therapeutic catheter, a termination catheter, a locking catheter, a cutting catheter, a diagnostic catheter, a tool catheter, or any other suitable catheter. These catheters will also be described in more detail below.

Other methods described here employ the use of various delivery catheters. For example, these methods generally comprise advancing a first delivery catheter to a first region of a body tissue, deploying a first anchor from the first delivery catheter, wherein the first anchor is attached to a guide element, proximally withdrawing the first delivery catheter, advancing a second delivery catheter over the guide element, and deploying a second anchor from the second delivery catheter.

These methods may deploy any number of anchors, and in some variations, the anchors are deployed into heart tissue, e.g., tissue in the region of the mitral valve. When multiple anchors are deployed to a region of the mitral valve annulus, the guide element the delivery catheters were advanced over, may be cinched, or pulled proximally to reduce the circumference of the mitral valve annulus. In this way, a mitral valve may be repaired using a relatively efficient and minimally invasive procedure. As an example, the use of a single guide element to deliver multiple delivery catheters and/or to deploy multiple anchors may result in reduced procedure time and a reduced likelihood of error in anchor placement. As another example, the use of a single anchored guide element may allow for the delivery of multiple delivery catheters and/or deployment of multiple anchors to a target site, without requiring visualization of the delivery and/or deployment. Furthermore, in some variations, the guide element may be fixedly attached or otherwise secured to a target site and used as a track for the delivery of multiple delivery catheters and/or deployment of multiple anchors to the target site, and also may be left at the target site when the procedure is finished, to serve as an implant itself.

Turning now to the figures, FIG. 1 is a cross-sectional schematic representation of a heart (100). As shown, heart (100) includes the superior vena cava (SVC), the right atrium (RA), the right ventricle (RV), the tricuspid valve leaflets (TVL), the aorta (A), the mitral valve leaflets (MVL), the left atrium (LA), and the left ventricle (LV). The tricuspid valve separates the right atrium (RA) from the right ventricle (RV), and the mitral valve separates the left atrium (LA) from the left ventricle (LV). The mitral valve has two leaflets (MVL), the anteromedial leaflet and the posterolateral leaflet. Surrounding the opening of the mitral valve is a fibrous ring known as the mitral valve annulus. A normally functioning mitral valve allows blood to flow into the left ventricle during ventricular diastole, and prevents blood from going from the ventricle to the left atrium during systole, in a retrograde fashion. A mitral valve that allows blood to flow into the left atrium is said to have regurgitation, and in instances where the regurgitation is severe, mitral valve repair may be desirable.

Figure 2:
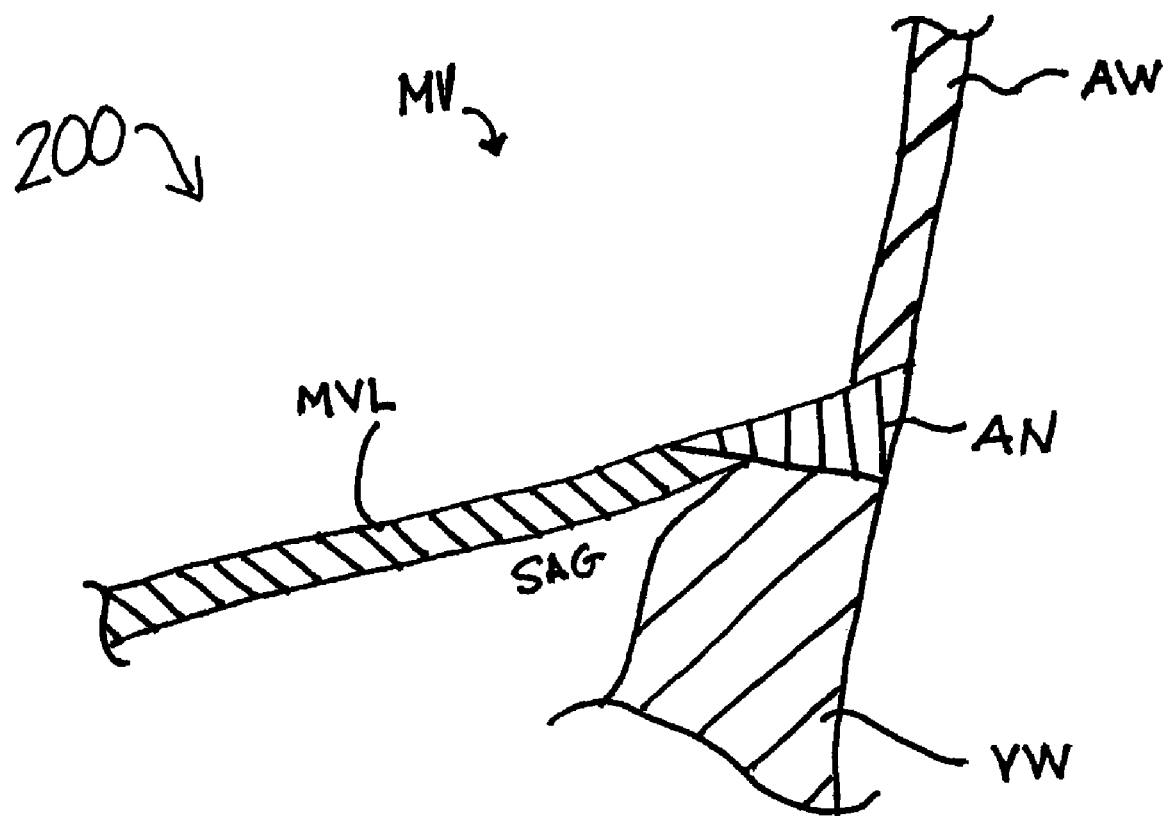
FIG. 2 is a cross-sectional view of a portion of a heart.

FIG. 2 provides a schematic cross-sectional view of a portion 200 of the mitral valve (MV) anatomy. As shown, portion (200) includes a mitral valve leaflet (MVL). The annulus (AN), which surrounds the valve, is also shown. As FIG. 2 shows, the SAG is the track defined by the joinder of the horizontal underside of the mitral valve annulus (AN) with the ventricular wall (VW). An equivalent subannular groove is positioned on the underside of the tricuspid valve, and the methods and devices described here may be used with respect to the tricuspid valve as well.

Any suitable method of accessing the SAG may be used. For example, a catheter may be inserted into the femoral artery and passed through the right atrium (RA), through the interatrial septum in the area of the foramen ovale behind the aorta (A), and into the left ventricle. Upon further advancement, the distal portion of the catheter will naturally travel under the posterolateral valve leaflet into the SAG. The catheter may be further advanced along the SAG, either partially or completely around the circumference of the valve. It is often desirable to have the catheter seated at the intersection of the mitral valve leaflets (MVL) and the ventricular wall, adjacent to, and very near the annulus from the underside. The use of a pre-shaped catheter (e.g., a catheter having a pre-shaped distal end or portion) may aid in placement by conforming to the target anatomy. While the approach described above employs access through the femoral artery, access may be obtained through other suitable vessels as well (e.g., the jugular artery).

FIG. 3A provides a flowchart depiction of a method (300) for deploying at least two anchors in the region of a heart valve annulus. As shown there, this illustrative method comprises advancing a guide catheter to the SAG (310), advancing a guidewire through a lumen of the guide catheter (320), advancing a tunnel catheter over the guidewire (330), and proximally withdrawing the guidewire from the tunnel catheter (340). After the guidewire has been proximally withdrawn, a first delivery catheter may be advanced through the lumen of the tunnel catheter (350) and a first anchor may be deployed into a first region of the heart valve annulus (360). The first anchor is typically fixedly attached or otherwise secured to a guide element, such as a tether. In this way, after the anchor is deployed, the guide element will remain attached to the anchor and the guide element may be used as a track or monorail for the advancement of additional delivery catheters thereover.

The guide element may be made from any suitable or desirable biocompatible material. The guide element may be braided or not braided, woven or not woven, reinforced or impregnated with additional materials, or may be made of a single material or a combination of materials. For example, the guide element may be made from a suture material (e.g., absorbable suture materials such as polyglycolic acid and polydioxanone, natural fibers such as silk, and artificial fibers such as polypropylene, polyester, polyester impregnated with polytetrafluoroethylene, nylon, etc.), may be made from a metal (absorbable or non-absorbable), may be made from a metal alloy (e.g., stainless steel), may be made from a shape memory material, such as a shape memory alloy (e.g., a nickel titanium alloy), may be made from combinations thereof, or may be made from any other biocompatible material. In some variations, when pulled proximally, the guide element will cinch or reduce the circumference of the mitral valve annulus. In certain variations, the guide element may be in the form of a wire. The guide element may include multiple layers, and/or may include one or more coatings. For example, the guide element may be in the form of a polymer-coated wire. In certain variations, the guide element may be formed of a combination of one or more sutures and one or more wires. As an example, the guide element may be formed of a suture that is braided with a wire. In some variations, the guide element may be formed of one or more electrode materials. In certain variations, the guide element may be formed of one or more materials that provide for the telemetry of information (e.g., regarding the condition of the target site).

In some variations, the guide element may include one or more therapeutic agents (e.g., drugs,.such as time-release drugs). As an example, the guide element may be partially or entirely coated with one or more therapeutic agents. In certain variations, the guide element may be used to deliver one or more growth factors and/or genetic regenerative factors. In some variations, the guide element may be coated with a material (e.g., a polymer) that encapsulates one or more therapeutic agents, or in which one or more therapeutic agents are embedded. The therapeutic agents may be used, for example, to treat the target site to which the guide element is fixedly attached or otherwise secured. In certain variations, the guide element may include one or more lumens through which a therapeutic agent can be delivered.

After the first anchor has been deployed in the region of the heart valve annulus, the first delivery catheter is withdrawn proximally and the tunnel catheter is positioned at a different location about the SAG (370). A second delivery catheter is then advanced over the guide element through the lumen of the tunnel catheter (380). During advancement of the second delivery catheter over the guide element, the guide element may enter the second delivery catheter through an opening at its distal end, and exit the second delivery catheter through an opening in its side wall that is proximal to its distal end. Alternatively, the guide element may enter the second delivery catheter through an opening at its distal end, and exit the second delivery catheter through an opening at its proximal end. After the second delivery catheter has been advanced over the guide element through the lumen of the tunnel catheter, a second anchor is deployed into a second region of the heart valve annulus (390).

Figure 3B:
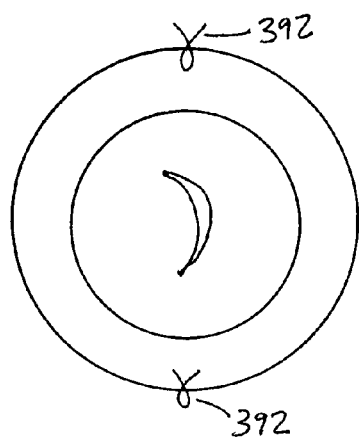
FIGS. 3B-3E schematically depict variations of anchor deployment.
Figure 3C:
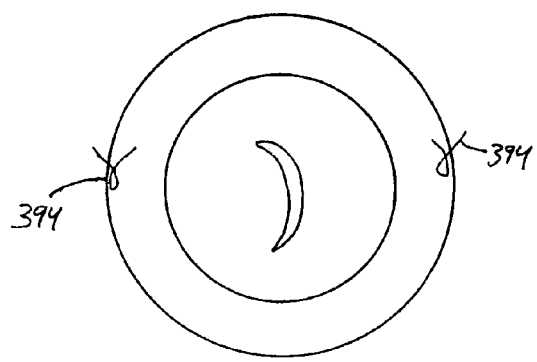
Figure 3D:
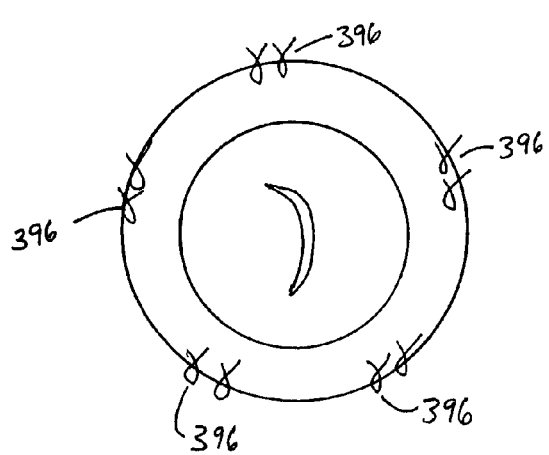
Figure 3E:
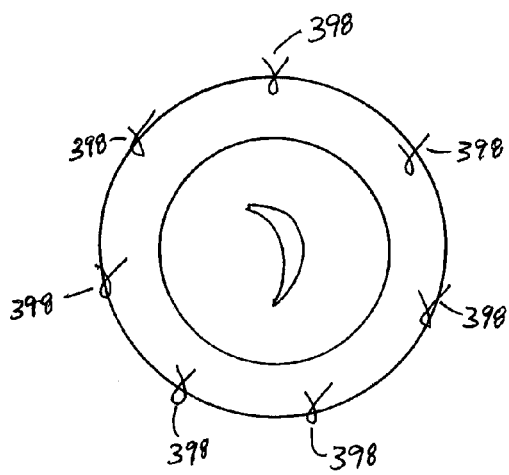

Any number of anchors may be deployed using this method with any number of suitable delivery catheters. For example, in some instances, it may be desirable to reduce the circumference of the mitral valve annulus by deploying two anchors in two different regions of the heart valve annulus, as shown by FIGS. 3B and 3C. FIGS. 3B and 3C (as well as FIGS. 3D and 3E below) depict the mitral valve (MV) of FIG. 2 schematically from an inferior perspective looking up. In FIG. 3B anchors (392) are shown deployed in the mitral valve in an anterior-posterior fashion, whereas in FIG. 3C anchors (394) are shown deployed in a transverse fashion. In other variations it may be desirable to deploy multiple sets of anchors about the mitral valve in the region of the annulus. For example, in FIG. 3D, pairs, or sets of two anchors (396) are shown deployed. It should be understood that any number of anchors, e.g., two, three, four, five, six, seven, etc. may make up a set, and that the sets need not be symmetrically or evenly spaced about the annulus as shown in FIG. 3D. Indeed, in some instances, it may be desirable to reinforce one anchor, but not others, and in these instances, there may be a combination of single and set anchor deployment. Again, the anchors (or sets of anchors) may be deployed symmetrically or evenly spaced about the annulus as shown in FIG. 3E with reference to anchors (398), but they need not be.

It should also be understood that while the method depicted in flowchart fashion in FIG. 3A shows multiple anchors being delivered via multiple delivery catheters, other methods of delivering the anchors may be used. For example, it some instances, it may be desirable to deliver multiple anchors from a single delivery catheter as described in more detail in U.S. patent application Ser. No. 11/201,949, which is hereby incorporated by reference in its entirety. Similarly, it may be desirable to combine multiple anchor delivery and deployment via a single delivery catheter with single anchor delivery and deployment via a single delivery catheter. Ordinary artisans will choose the number and type of catheters most appropriate for their procedure and circumstances.

Figure 4A:
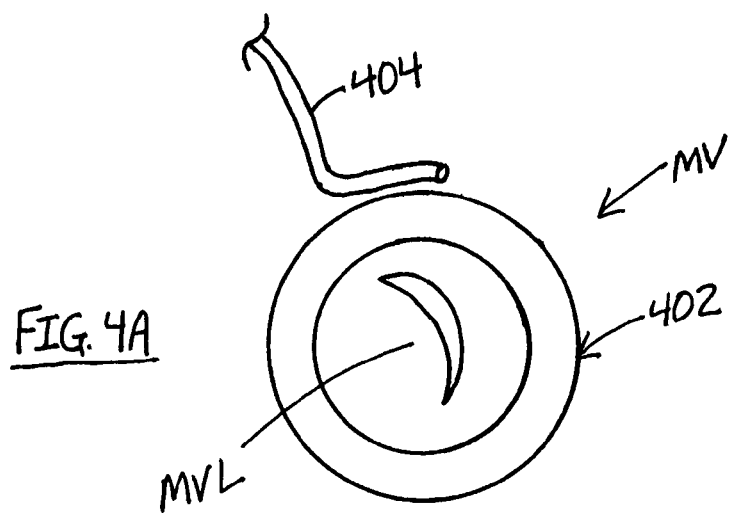
FIGS. 4A-4I provide a detailed depiction of a method for advancing at least two delivery catheters to the sub-annular groove ("SAG") of a heart valve to deliver at least two anchors into a region of a heart valve annulus.
Figure 4B:
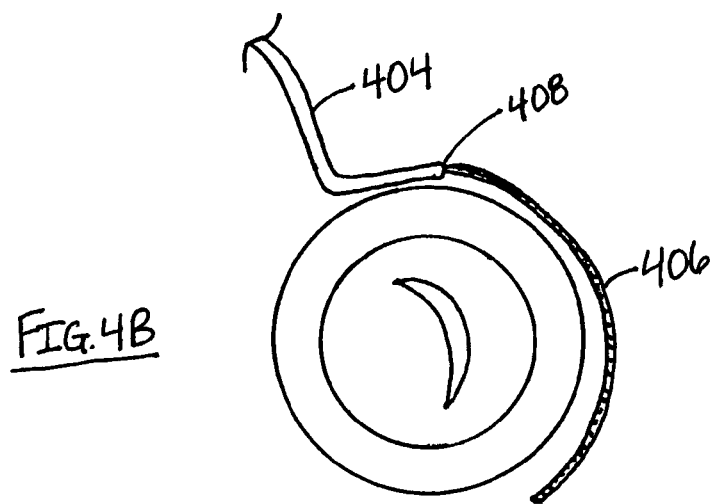

FIGS. 4A-4I provide a more detailed depiction of the method shown in flowchart form in FIG. 3A. In FIGS. 4A-4I, the mitral valve (MV) of FIG. 2 is depicted schematically from an inferior perspective looking up. Referring to FIG. 4A, a guide catheter (404) is advanced to SAG (402) using any of the access routes (or any other suitable access routes) previously described. After guide catheter (404) has been positioned at the desired location in SAG (402), a guidewire (406) is advanced through the lumen of guide catheter (404). Guidewire (406) is advanced beyond the distal end (408) of guide catheter (404), so that guidewire (406) extends further along SAG (402) than guide catheter (404), as shown in FIG. 4B.

Figure 4C:
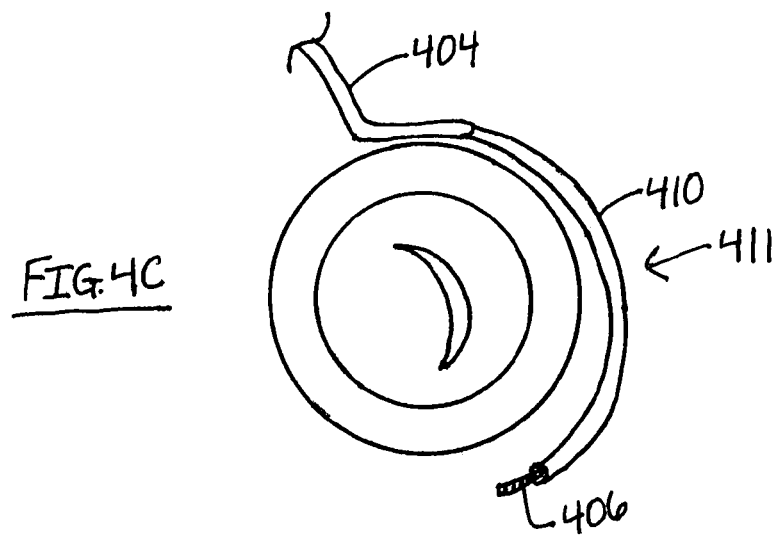

After guidewire (406) has been positioned in the SAG, a tunnel catheter (410) is advanced through guide catheter (404), over guidewire (406), which is shown in FIG. 4C. Tunnel catheter (410) may be any suitable catheter, and in some instances, as discussed above, it is desirable that the tunnel catheter be pre-shaped or pre-formed at its distal end, such as the tunnel catheter illustrated in FIG. 4C. As shown there, the tunnel catheter has a pre-shaped distal portion comprising a curve. In this way, the tunnel catheter may more easily conform to the geometry of the mitral valve. It should also be understood that while one distal curve is shown, any of the catheters or guidewires described here may be pre-shaped or pre-formed to include any number of suitable curves. Of course, the guidewires and/or catheters described here may also be steerable.

Figure 13A:
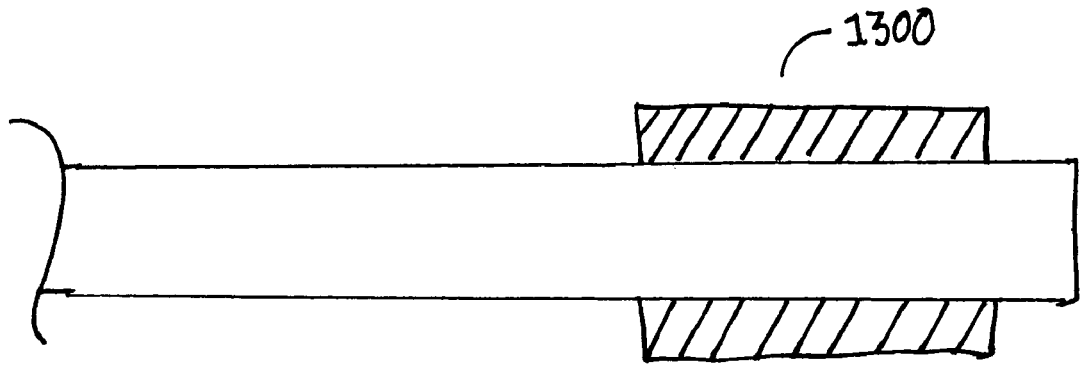
FIGS. 13A-13C depict various expandable members that may be used to help stabilize a catheter in the SAG.
Figure 13B:
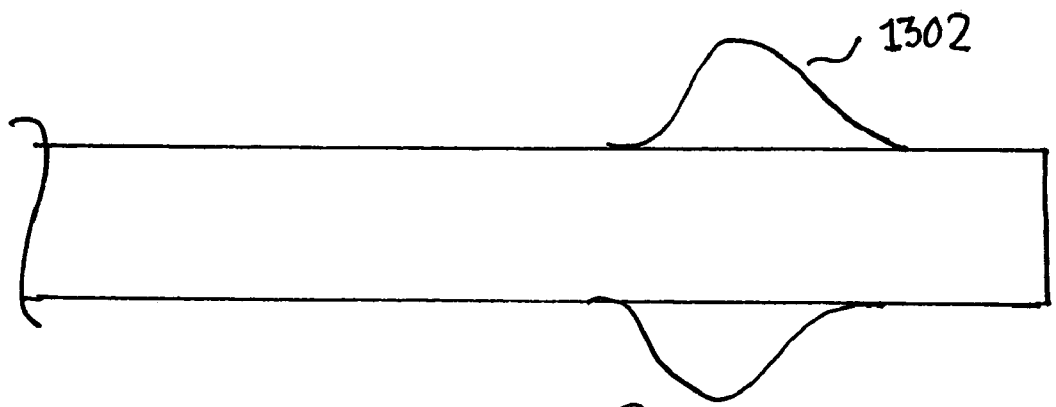
Figure 13C:
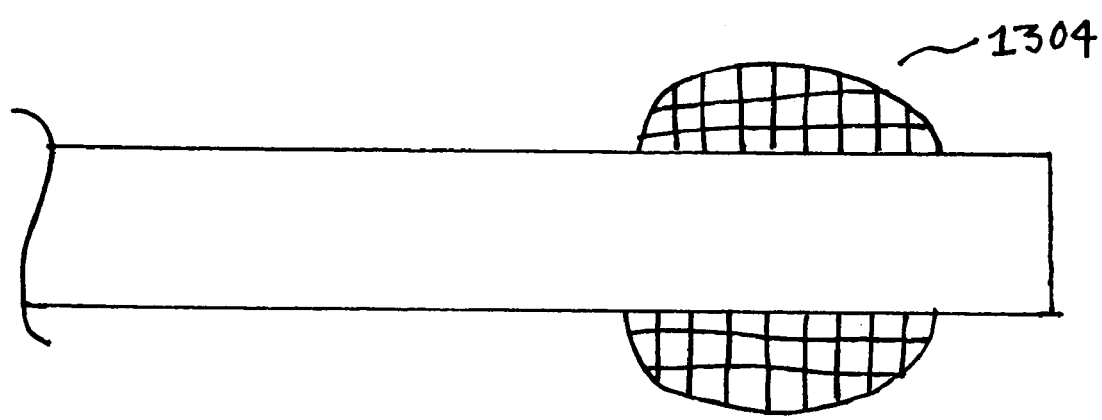

The tunnel catheter may also comprise an expandable member configured to stabilize the catheter with respect to the SAG. For example, the expandable member may be configured to engage against a first portion of tissue in order to stabilize the catheter with respect to a second portion of tissue. The expandable member may be any suitable expandable member. For example, it may be a low-pressure balloon (1300), as shown in FIG. 13A. The low-pressure balloon may be made of a compliant material such as silicone, urethane, natural latex, polyisoprene or other rubbers or rubber copolymers/blends (e.g., styrenic block copolymers, polyolefin blends, polyurethane alloys, etc.), combinations or blends thereof, or other suitable compliant materials known in the art. In some variations, an elastomeric polyurethane alloy is used. The expandable member may also be made of a shape memory material such as a nickel titanium alloy, and have the shape of a wing or an arm (1302), as shown in FIG. 13B, or a basket (1304), as shown in FIG. 13C.

In some variations, the expandable member is a low-pressure compliant balloon, inflatable with a pressurized solution (e.g., saline, or saline in combination with a contrast agent, such as a 75%/25% mixture of saline to contrast). The pressurized solution may be delivered to the balloon via a separate infusion lumen. The infusion lumen may be concentric with the lumen through which the delivery catheters are advanced, but need not be. For example, the infusion lumen may also be located along one or both sides of the tunnel catheter. The size of the expandable member will depend upon the particular body tissue to be stabilized, but in the case of SAG stabilization, a half-inch long to an inch-long balloon may be appropriate. One or both sides of the balloon may be inflated, but in instances of SAG stabilization, it is more desirable to inflate only that side opposite the SAG. In this way, the tunnel catheter is pushed and held in greater apposition with the SAG. Similarly, the balloon may be made to inflate with variable stiffness or rigidity along its length for better apposition against certain portions of tissue.

Figure 4D:
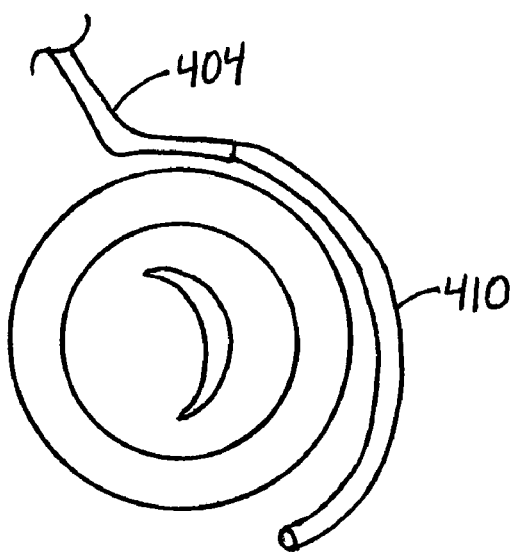
Figure 4E:
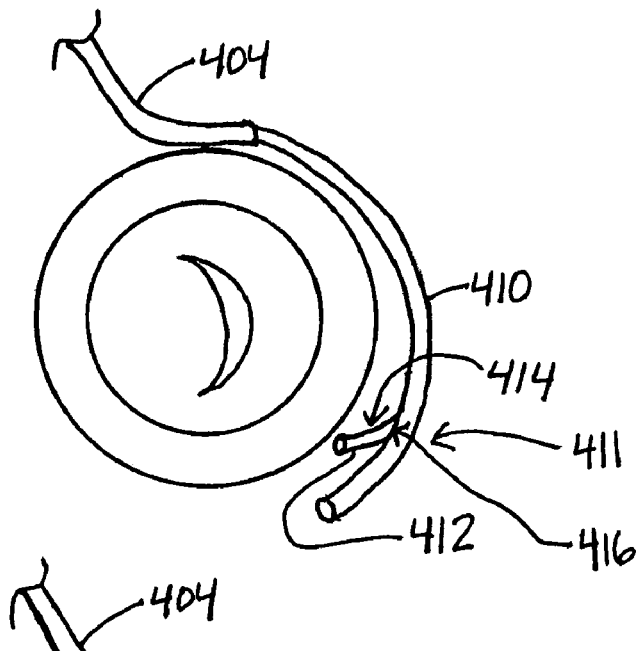
Figure 4F:
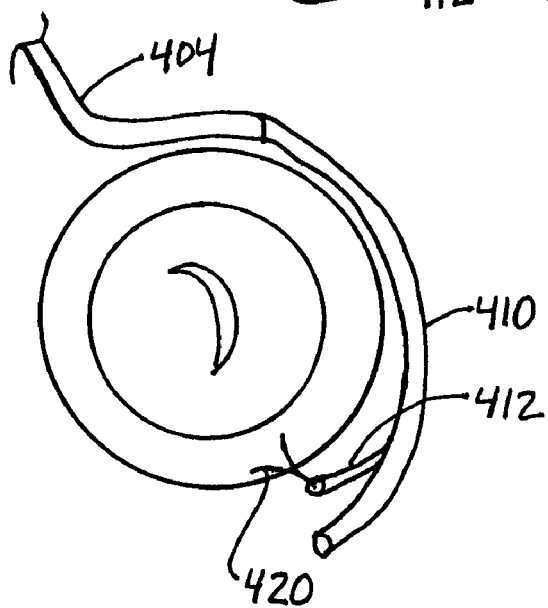

After tunnel catheter (410) has been positioned in the SAG, guidewire (406) is withdrawn proximally as shown in FIG. 4D. After guidewire (406) has been withdrawn, a delivery catheter (412) may then be advanced through the lumen of the tunnel catheter (410). As shown in FIG. 4E, a distal portion (414) of delivery catheter (412) is advanced through an opening (416) in distal portion (411) of tunnel catheter (410). Next, and as shown in FIG. 4F, an anchor (420), which is attached to a guide element (shown in FIG. 4G as a tether (422)), is deployed from delivery catheter (412). The anchor may be deployed from the delivery catheter in any suitable fashion, as will be described in more detail below when more detail is focused on the delivery catheter. For example, the anchor may be deployed using a push-pull wire (e.g., by pushing the wire distally or pulling the wire proximally), using a plunger, or may be deployed with any other suitable actuation technique. Similarly, anchor (420) may be attached to tether (422) by any suitable attachment method. For example, one or more knots, welded regions, and/or adhesives may be used.

The anchors for use with the methods and devices described here may be any suitable anchor. The anchors may be made of any suitable material, may be any suitable size, and may be of any suitable shape. The anchors may be made of one material or more than one material. Examples of anchor materials include super-elastic or shape memory materials, such as nickel-titanium alloys and spring stainless steel. Examples of anchor shapes include T-tags, rivets, staples, hooks (e.g., C-shaped or semicircular hooks, curved hooks of other shapes, straight hooks, barbed hooks), multiple looped anchors, and clips. The anchors may be configured to self-expand and self-secure into tissue, but need not be configured in such a fashion. Additionally, while the delivery and deployment of multiple anchors of the same shape over a single guide element have been described, in some variations, a single guide element can be used to deliver and deploy multiple anchors having different shapes. Similarly, in certain variations, a single guide element can be used in the delivery and deployment of multiple anchors having different sizes. Illustrative examples of suitable anchors are described in more detail, for example, in U.S. patent application Ser. No. 11/202,474, which is hereby incorporated by reference in its entirety.

Anchor (420), shown in FIG. 4F, self-expands as it exits delivery catheter (412) and self-secures into a region of the mitral valve annulus (AN). It should be understood that the anchors may be deployed into the annular tissue directly, or slightly below the annular tissue in the vicinity of the SAG.

Figure 4G:
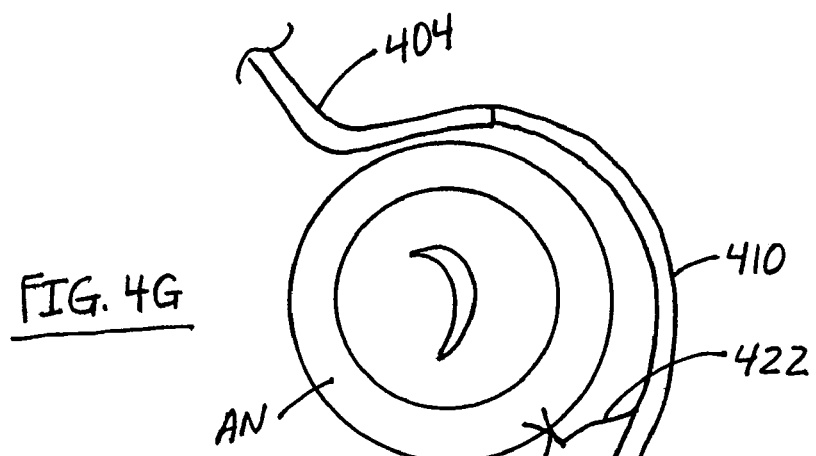
Figure 4H:
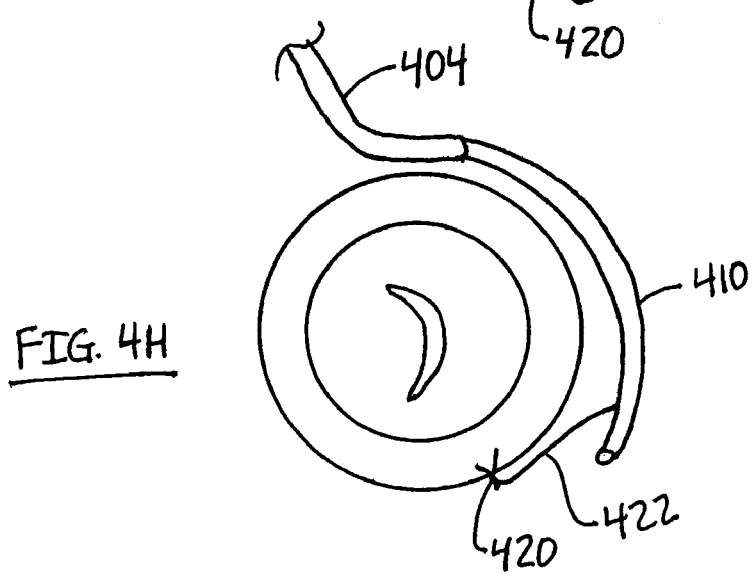
Figure 4I:
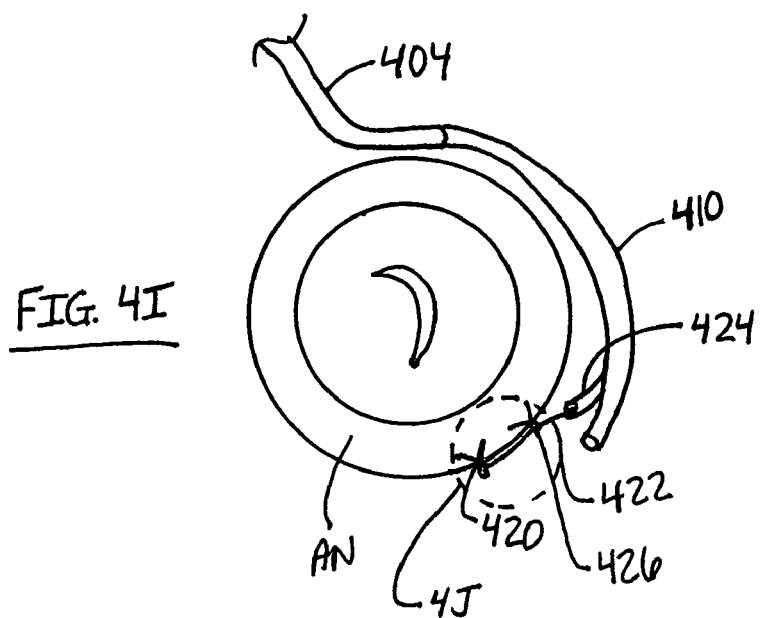

After anchor (420) has been deployed, delivery catheter (412) is proximally withdrawn. FIG. 4G shows anchor (420), attached to tether (422) and secured to the mitral valve annulus (AN). As shown in FIG. 4H, tunnel catheter (410) is now moved to a different location or position in the SAG, and a second delivery catheter (424) is advanced through the lumen of tunnel catheter (410), over tether (422), as shown in FIG. 4I.

Figure 5A:
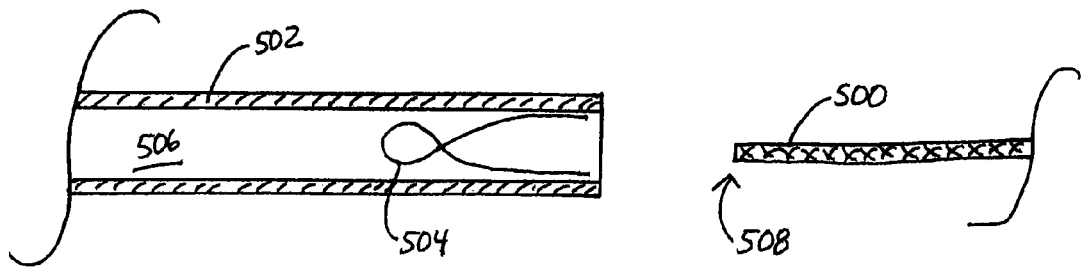
FIGS. 5A-5D illustrate a method for engaging a guide element with an anchor.

Before delivery catheter (424) is advanced through tunnel catheter (410), tether (422) is threaded into delivery catheter (424), and is slidably engaged with a second anchor (426). Any of a number of different methods can be used to thread a guide element, such as a tether, into a delivery catheter, and to engage the guide element with an anchor. For example, FIGS. 5A-5D show a method that includes using a lasso to thread a tether into a delivery catheter, and to slidably engage the tether with an anchor. By using the lasso, the amount of time it takes to thread the tether into the delivery catheter and anchor can be reduced. As shown in FIG. 5A, an anchor (504) is pre-loaded into a lumen (506) of a delivery catheter (502), and the proximal end (508) of a tether (500) is in the proximity of delivery catheter (502). Next, and referring to FIG. 5B, a lasso (510) is introduced into lumen (506). Lasso (510) is threaded through an eyelet (512) of anchor (504), and is used to engage tether (500), as shown in FIG. 5C. Referring now to FIG. 5D, lasso (510) is withdrawn proximally, thereby pulling tether (500) through eyelet (512).

Figure 5B:
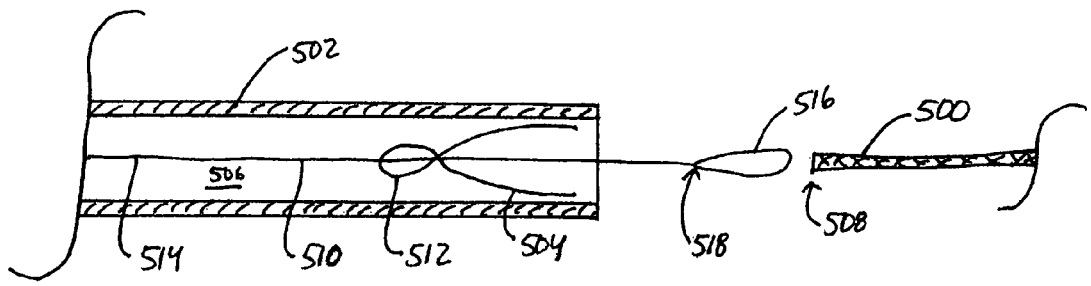
Figure 5C:
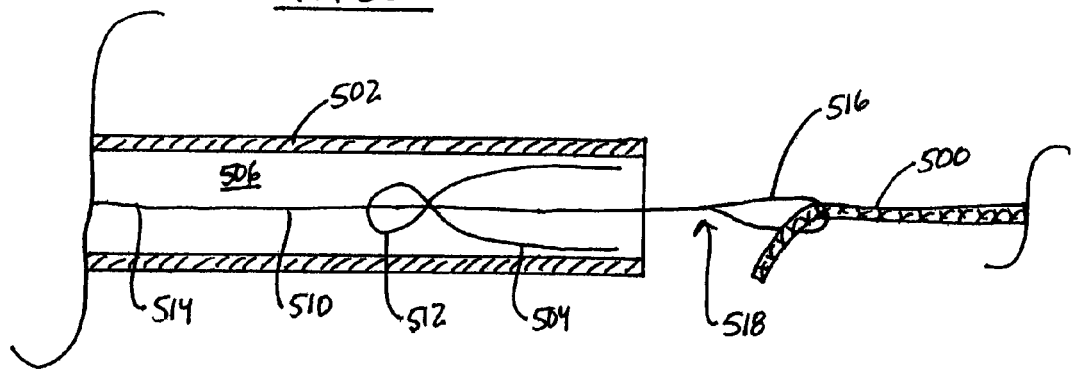
Figure 5D:
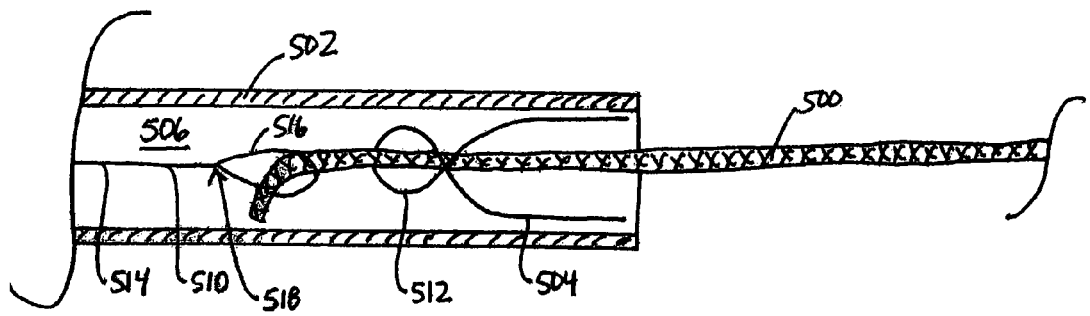
Figure 6A:
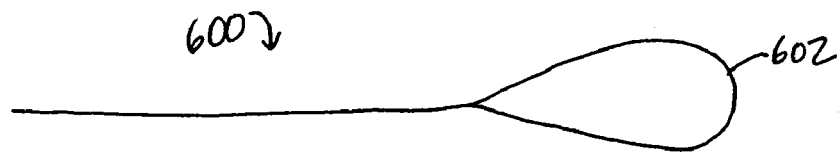
FIGS. 6A-6F depict different variations of lassos.
Figure 6B:
Figure 6C:
Figure 6D:
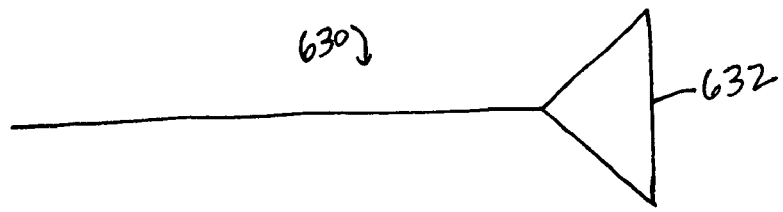
Figure 6E:
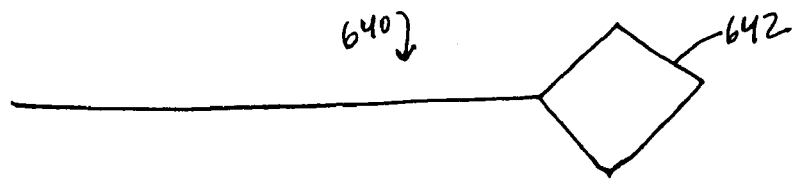
Figure 6F:
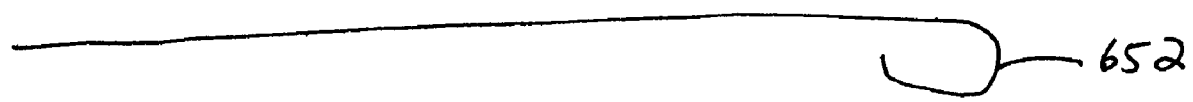

As shown in FIGS. 5B-5D, lasso (510) includes a wire portion (514) and a loop (516) at the distal end (518) of the wire portion. While loop (516) is shown as generally rounded in shape, in some variations, a lasso can include a loop having a different shape. For example, FIGS. 6A-6F show lassos having differently shaped loops. More specifically, FIG. 6A shows a lasso (600) with a substantially symmetrical round loop (602), FIG. 6B shows a lasso (610) with an asymmetrical round loop (612), FIG. 6C shows a lasso (620) with a square loop (622), FIG. 6D shows a lasso (630) with a triangular loop (632), and FIG. 6E shows a lasso (640) with a diamond-shaped loop (642). Additionally, while closed loops have been shown for engaging guide elements, in some variations, a lasso may include an open guide element-engaging structure, such as a hook. For example, FIG. 6F shows a lasso (650) with a hook (652) at one end that can be used to engage a guide element. The shape of a lasso's guide element-engaging structure may be selected based on the configuration of the catheter through which the lasso is being threaded, and/or the type of guide element that is being threaded.

A lasso can be formed of, for example, a wire including one or more metals, metal alloys (e.g., nickel-titanium alloys), and/or polymers. The wire can have a circular cross-section or a non-circular cross-section. The lasso's guide element-engaging structure and wire portion may be formed from the same material or different materials. In some variations, the guide element-engaging structure is integrally formed with the wire portion. In other variations, the guide element-engaging structure is attached (e.g., welded) to the wire portion. The lasso or a portion of the lasso (e.g., the loop) can be relatively flexible. This flexibility may help the lasso to more readily engage the guide element by allowing the lasso to flex and bend around the guide element. In certain variations, at least a portion of a lasso can be formed of a wire that is covered with a sheath, such as a polymer sheath, and/or a coating, such as a polymer coating. The presence of the sheath or coating may enhance the passage of the lasso through a delivery catheter lumen.

While FIGS. 5A-5D show a method that includes using a lasso to thread a tether through a delivery catheter and an anchor, the method can also be used to thread guide elements, such as tethers, through other types of catheters (e.g., guide catheters, sheaths, drug delivery catheters, therapeutic catheters, locking catheters, diagnostic catheters, tool catheters, cutting catheters) and/or implants.

Figure 7A:
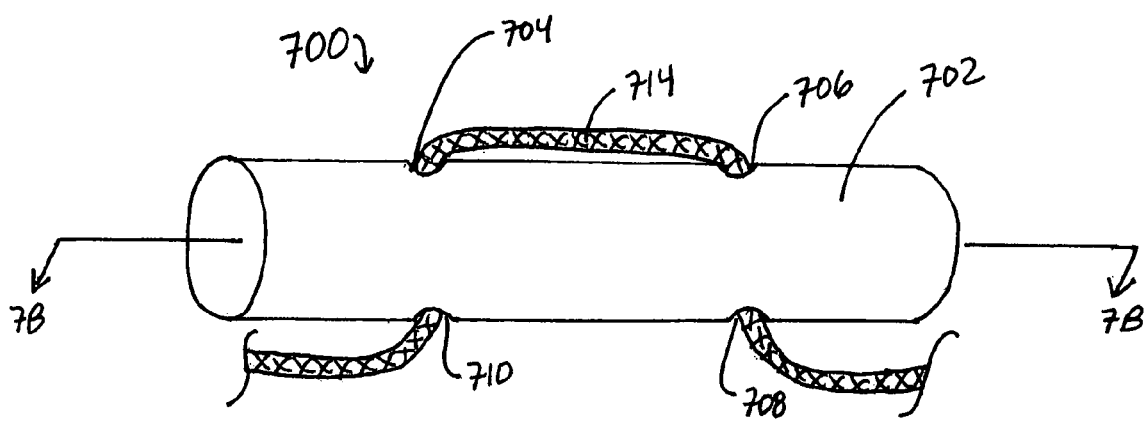
FIG. 7A is a perspective view of a locking catheter.
Figure 7B:
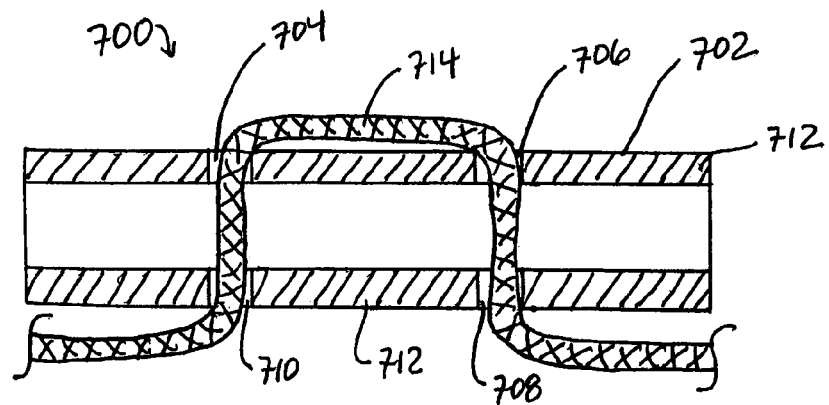
FIG. 7B is a cross-sectional view of the locking catheter of FIG. 7A, taken along line 7B-7B.

As an example, FIGS. 7A and 7B show a locking catheter (700) including a tubular member (702) having a wall (712) with four openings (704, 706, 708, and 710) formed in it. Locking catheters may be used to maintain tension in a guide element, such as a tether, once the guide element has been cinched (as described in further detail below), and to stabilize the guide element for cutting. In FIGS. 7A and 7B, a tether (714) has been threaded into locking catheter (700), through holes (704, 706, 708, and 710). The tether may be threaded into the locking catheter using, for example, a lasso, such as one of the lassos described above. The lasso may have a relatively flexible loop which may enhance the maneuverability of the lasso through the holes in the locking catheter. While locking catheter (700) is shown as including four holes through which tether (714) is threaded, locking catheters can include other numbers of holes. For example, some variations of locking catheters may include fewer holes (e.g., two holes), while other variations of locking catheters may include more holes (e.g., six holes, eight holes, etc.). As the number of holes in a locking catheter increases, the likelihood of movement by a guide element that is threaded through the holes may decrease.

While one variation of a threading method is shown in FIGS. 5A-5D, other variations of threading methods may be used. For example, in some variations, a threading device, such as a threading rod, may be used to thread a guide element through a catheter. The guide element may be threaded around a groove in the threading rod, and/or may be threaded through one or more holes and/or lumens in the threading rod. The threading rod can provide support to the guide element, thereby making it easier to thread the guide element into the catheter. This, in turn, can reduce the total guide element-threading time. Threading devices are described, for example, in U.S. patent application Ser. No. 11/232,190, which is hereby incorporated by reference in its entirety.

Figure 8A:
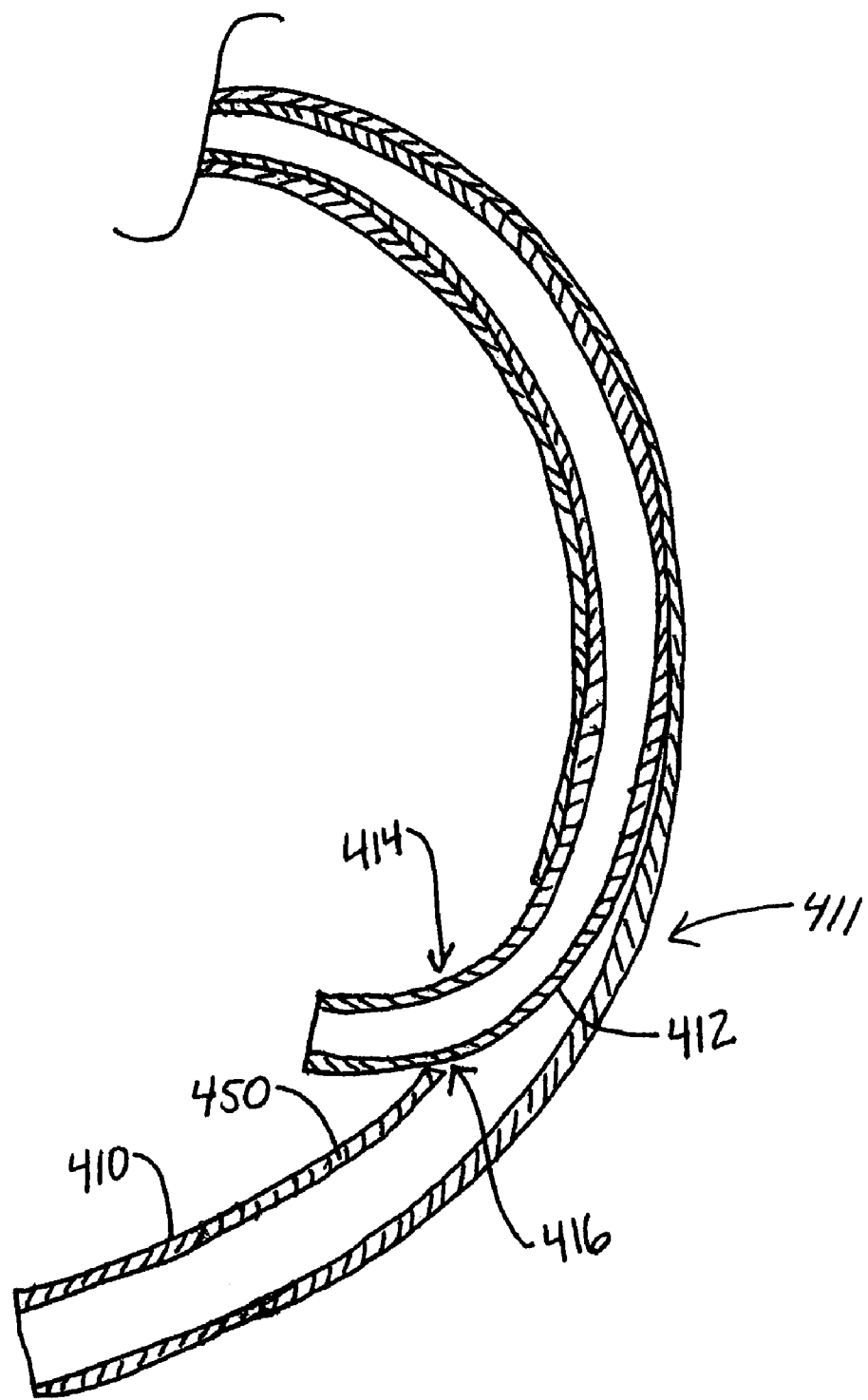
FIG. 8A is a cross-sectional view of a portion of a tunnel catheter through which a delivery catheter is advanced.

With reference now to FIGS. 8A and 4I, after delivery catheter (424) has been advanced through tunnel catheter (410), delivery catheter (424) is advanced through opening (416) in distal portion (411) of tunnel catheter (410), and is used to deploy anchor (426).

Figure 8B:
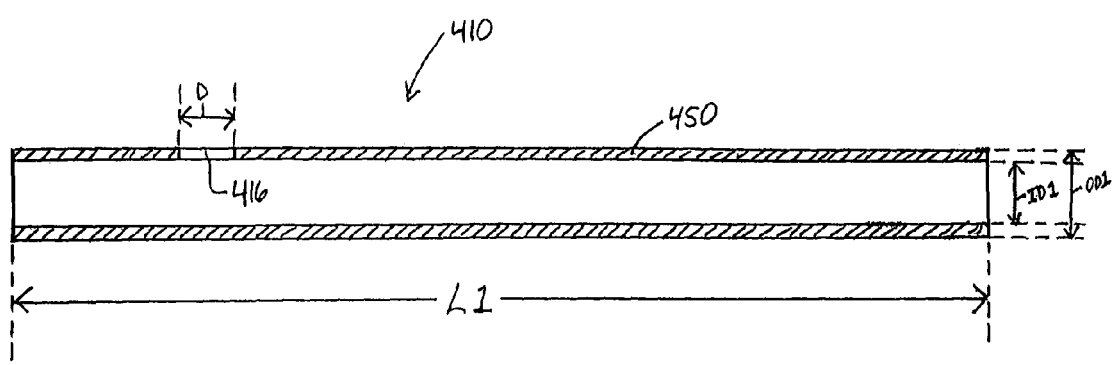
FIG. 8B is a side cross-sectional view of the tunnel catheter of FIG. 8A.

FIG. 8B shows a cross-sectional view of tunnel catheter (410), straightened to show its dimensions. Opening (416), which is formed in a wall (450) of tunnel catheter (410), can be circular or non-circular. As shown in FIG. 8B, opening (416) has a dimension (D) which may be a length, a width, or a diameter of the opening. In some variations, such as when dimension (D) is a width of the opening, dimension (D) may be from about 0.08 inch to about 0.09 inch. In certain variations, such as when opening (416) is circular and dimension (D) is a diameter of the opening, dimension (D) may be from about 0.09 inch to about 0.15 inch. In some variations, such as when dimension (D) is a length of the opening, dimension (D) may be from about 0.15 inch to about 0.2 inch. Opening (416) may be formed in wall (450) using, any suitable technique, for example, with use of a laser.

As shown in FIG. 8B, tunnel catheter (410) has an inner diameter (ID1), an outer diameter (OD1), and a length (L1). Length (L1) may measure, for example, from about 46 inches to about 48 inches. In some variations, inner diameter (ID1) may be from about 0.085 inch to about 0.1 inch. Inner diameter (ID1) may be selected, for example, based on the dimensions of delivery catheter (424). As an example, if delivery catheter (424) has a relatively large outer diameter, then inner diameter (ID1) may also be relatively large, to provide for relatively rapid advancement of delivery catheter (424) through tunnel catheter (410). In some variations, outer diameter (OD1) may be from about 0.135 inch to about 0.15 inch. Outer diameter (OD1) may be selected, for example, based on the planned path for advancement of tunnel catheter (410) to the target tissue.

Tunnel catheter (410) can be formed of any of a number of different materials. Examples of suitable materials include polymers, such as polyether-block co-polyamide polymers, copolyester elastomers, thermoset polymers, polyolefins (e.g., polypropylene or polyethylene, including high-density polyethylene and low-density polyethylene), polytetrafluoroethylene, ethylene vinyl acetate, polyamides, polyimides, polyurethanes, polyvinyl chloride (PVC, fluoropolymers (e.g., fluorinated ethylene propylene, perfluoroalkoxy (PFA) polymer, polyvinylidenefluoride, etc.), polyetheretherketones (PEEKs), and silicones. Examples of polyamides that may be included in tunnel catheter (410) include Nylon 6 (e.g., Zytel® HTN high performance polyamides from DuPont™), Nylon 11 (e.g., Rilsan® B polyamides from Arkema Inc.), and Nylon 12 (e.g., Grilamide polyamides from EMS-Grivory, Rilsan® A polyamides from Arkema Inc., and Vestamid® polyamides from Degussa Corp.). In some variations, tunnel catheter (410) may be formed of multiple polymers. For example, tunnel catheter (410) may be formed of a blend of different polymers, such as a blend of high-density polyethylene and low-density polyethylene. While wall (450) of tunnel catheter (410) is formed of a single layer, some variations of tunnel catheters may include walls having multiple layers (e.g., two layers, three layers). Furthermore, some variations of tunnel catheters may include at least two sections that are formed of different materials and/or that include different numbers of layers. Additionally, certain variations of tunnel catheters may include multiple (e.g., two, three) lumens. The lumens may, for example, be lined and/or reinforced (e.g., with braiding).

Figure 14A:
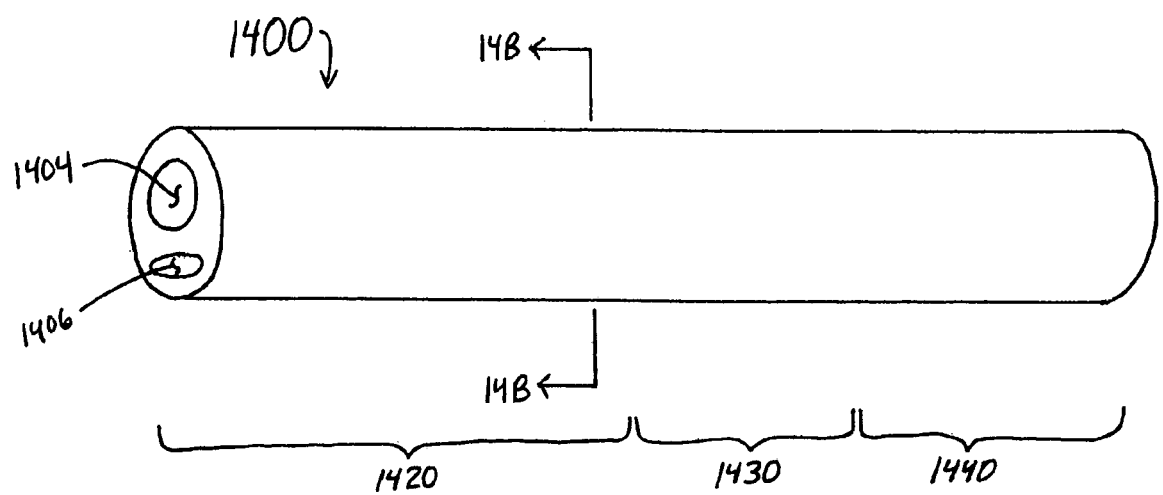
FIG. 14A is a perspective view of a tunnel catheter.
Figure 14B:
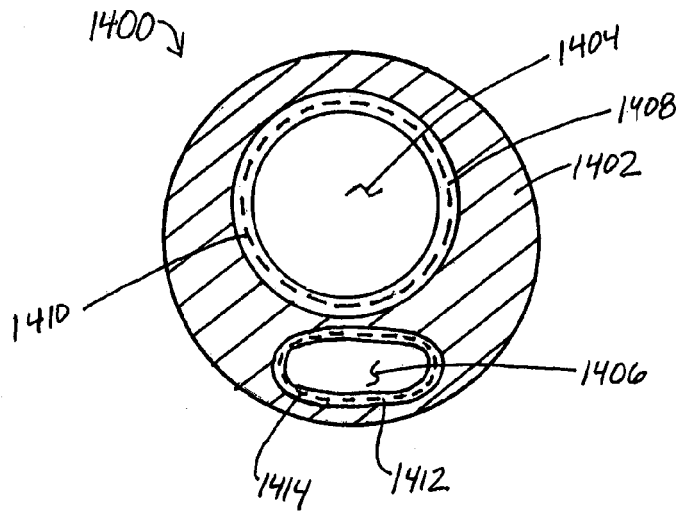
FIG. 14B is a cross-sectional view of the tunnel catheter of FIG. 14A, taken along line 14B-14B.

For example, FIGS. 14A and 14B shows a tunnel catheter (1400) having multiple lumens. As shown, tunnel catheter (1400) includes a body (1402) having a proximal section (1420), a transition section (1430), and a distal section (1440), and defining a primary lumen (1404) and a secondary lumen (1406). In some variations, primary lumen (1404) may be used to advance a delivery catheter to a target tissue, while secondary lumen (1406) may be used as an inflation lumen. For example, secondary lumen (1406) may be injected with a mix of 25% contrast agent and 75% heparinized saline to inflate a balloon carried by the tunnel catheter. Primary lumen (1404) is lined with a liner (1408) including a braided reinforcement (1410), and secondary lumen (1406) is similarly lined with a liner (1412) including a braided reinforcement (1414).

Body (1402) may be formed of one or more materials, such as one or more polymers. For example, in some variations, proximal section (1420) of body (1402) may be formed of a blend of high-density polyethylene (HDPE) and low-density polyethylene (LDPE), transition section (1430) of body (1402) may be formed of DuPont™ 20 low-density polyethylene (from DuPont™), and distal section (1440) may be formed of Elvax™ 450 ethylene vinyl acetate (from DuPont™). In such variations, proximal section (1420) may be about 28 inches long, transition section (1430) may be about eight inches long, and distal section (1440) may be about ten inches long. However, other lengths may be used for the proximal, transition, and distal sections.

Liner (1408) may be formed of high-density polyethylene or polytetrafluoroethylene (e.g., etched polytetrafluoroethylene), and liner (1412) may be formed of a flattened polyimide.

Braided reinforcements (1410) and (1414) may be formed of the same material or different materials. An example of a material that may be suitable for one or both of the braided reinforcements is stainless steel, such as 304V stainless steel.

Figure 9:
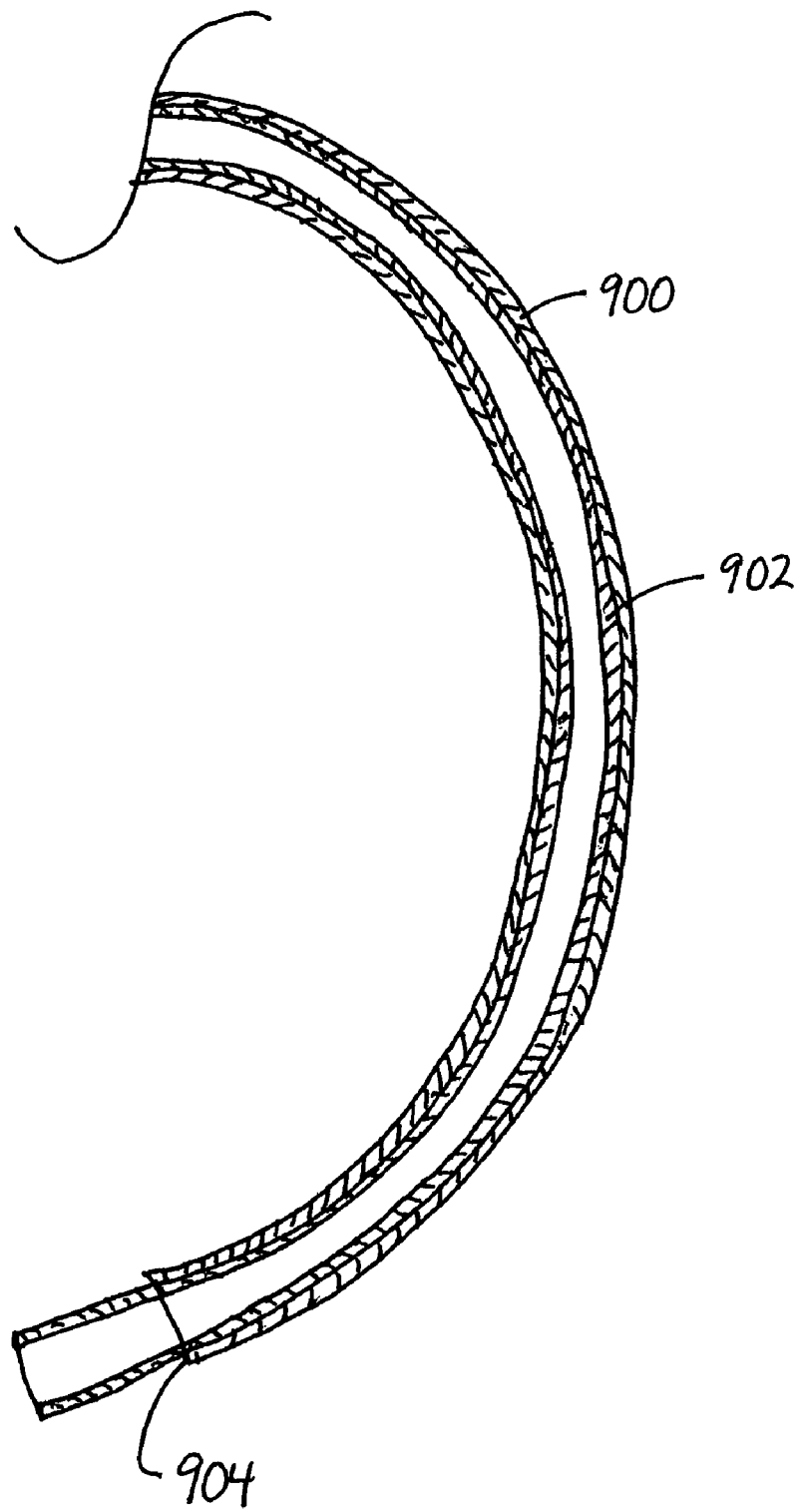
FIG. 9 is a cross-sectional view of a portion of a tunnel catheter through which a delivery catheter is advanced.

While FIGS. 8A and 8B show one variation of a tunnel catheter, it should be understood that other variations of tunnel catheters can be used for advancing a delivery catheter to a target site as well. For example, FIG. 9 shows a tunnel catheter (900), where a delivery catheter (902) is advanced out and through the distal end (904) of tunnel catheter (900).

Figure 8C:
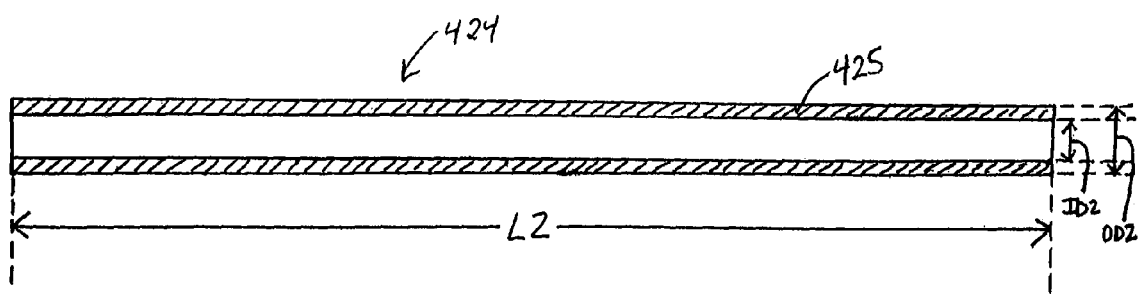
FIG. 8C is a side cross-sectional view of the tunnel catheter of FIG. 8A.

FIG. 8C provides a cross-sectional view of delivery catheter (424), straightened to show its dimensions. As shown in FIG. 8C, delivery catheter (424) has an inner diameter (ID2), an outer diameter (OD2), and a length (L2). Length (L2) may be, for example, from about 120 centimeters to about 150 centimeters. In some variations, inner diameter (ID2) may be from about 0.045 inch to about 0.06 inch. Inner diameter (ID2) can be selected, for example, based on the sizes and/or types of anchors being deployed from the delivery catheter. In certain variations, outer diameter (OD2) may be from about 0.07 inch to about 0.095 inch.

Delivery catheter (424) can be formed of any of a number of different materials. Examples of suitable materials include polymers, such as the polymers described above with reference to tunnel catheter (410), metals (e.g., platinum, gold), metal alloys (e.g., nickel-titanium alloys such as Nitinol), and combinations of these materials. Delivery catheter (424) may be formed of some or all of the same materials as tunnel catheter (410), or may be formed of different materials from tunnel catheter (410). While delivery catheter (424) is shown as including a wall (425) that is formed of one layer, some variations of delivery catheters may include walls that are formed of multiple layers. Furthermore, delivery catheters may include at least two sections that are formed of different materials and/or that include different numbers of layers.

While FIG. 8C shows one variation of a delivery catheter, any of a number of different types and configurations of delivery catheters can be used for implant delivery. A delivery catheter can have one lumen or multiple (e.g., two, three) lumens. In some variations, one section of a delivery catheter can have fewer lumens than another section of the delivery catheter. For example, a distal section of a delivery catheter may have one lumen, while a proximal section of the delivery catheter may have two or three lumens. The lumens in a delivery catheter may be, for example, guide element lumens and/or infusion lumens (e.g., for the infusion of one or more therapeutic agents into a target tissue). The lumens may be located in a variety of different regions of the delivery catheter. For example, a delivery catheter may include a generally tubular member and a lumen formed on a surface of the generally tubular member. The lumens in a delivery catheter may extend along the length of the delivery catheter, may be shorter than the delivery catheter, or may be a combination of the two. Furthermore, a lumen may be located only in a distal section of a delivery catheter, or only in a proximal section of a delivery catheter. Additionally, certain variations of delivery catheters, or other types of catheters, may include other structures through which a guide element can be threaded. As an example, some variations of delivery catheters may include slotted regions on their outer surfaces. The slotted regions may be used, for example, to thread the delivery catheters over a guide element.

FIGS. 12A-12D show different detailed views of a variation of a delivery catheter (1200) that can be used to deliver one or more anchors to a target site. As shown in FIG. 12A, delivery catheter (1200) has a distal region (1204) including a tip (1202), an anchor-holding region (1206) including a primary lumen (1208), an intermediate region (1210) including both primary lumen (1208) and a secondary lumen (1212), and a proximal region (1214) including primary lumen (1208). An anchor (1216) is disposed within primary lumen (1208), in the anchor-holding region (1206). While only one anchor is shown in the anchor-holding region, some variations of delivery catheters may include an anchor-holding region that is adapted to hold multiple anchors. Similarly, while the variation shown in FIGS. 12A-12D depict anchors adapted to be deployed from the distal end of the delivery catheter, it should be understood that the anchors may be deployed from any suitable region of the delivery catheter, as desirable. For example, if desirable, the anchor may be delivered out of a side port or hole on the delivery catheter.

As shown in FIGS. 12A-12D, a tether (1218) is threaded into a slot (1219) of tip (1202) (shown in FIGS. 12C and 12D), and through an eyelet (1226) of anchor (1216). After extending through the eyelet, the tether exits primary lumen (1208), and extends along an exterior surface (1221) of delivery catheter (1200) for the remainder of the length of the anchor-holding region, as shown in FIG. 12C. The tether then enters secondary lumen (1212), and extends through the length of the secondary lumen, exiting the secondary lumen at an end of distal region (1214). An actuator (1220) is slidably disposed within primary lumen (1208), and can be used to deploy anchor (1216). The actuator is in the form of a pushable generally tubular member, although other forms of actuators may be used. For example, in some variations, a solid rod may be used as an actuator.

A retrieval suture (1224) is slidably disposed within actuator (1220), and extends past the distal end (1222) of the actuator. The retrieval suture loops through eyelet (1226) of anchor (1216), so that it is engaged with anchor (1216). In this way, anchors that have been misfired or misplaced may be retrieved proximally within delivery catheter (1200) for redeployment. The retrieval suture is also, of course, capable of being disengaged from anchor (1216) after appropriate placement of the anchor. In some variations, the retrieval suture may be disengaged from the anchor by pulling on the proximal end of the retrieval suture and withdrawing the retrieval suture from the anchor eyelet and the catheter. Retrieval suture (1224) may be formed of, for example, any of the tether materials described above. Furthermore, while a delivery catheter including a retrieval suture has been described, in some variations, a delivery catheter may not include a retrieval suture, or may include multiple retrieval sutures.

As it exits delivery catheter (424), anchor (426) self-expands and self-secures to tissue in the region of the mitral valve annulus (AN). Returning now to earlier figures, as shown in FIG. 4I, anchor (426) self-secures to a different region of the mitral valve annulus from anchor (420).

Figure 4J:
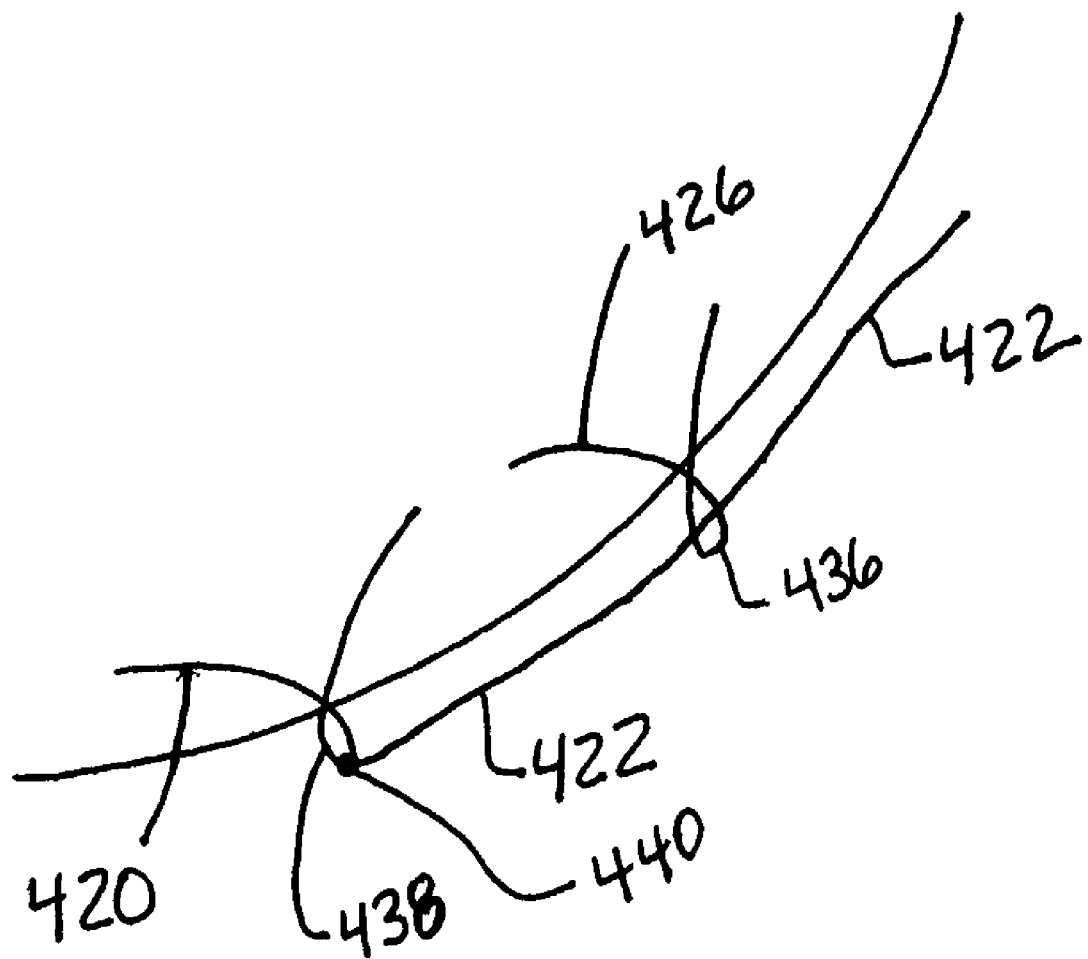
FIG. 4J is an enlarged view of region 4J of FIG. 4I.

FIG. 4J shows that while anchor (420) is fixedly attached to tether (422), anchor (426) is slidably coupled to tether (422). More specifically, anchor (420) includes an eyelet (438) that is fixedly attached to the tether at an attachment point (440), and anchor (426) includes an eyelet (436) through which the tether is threaded. The threading of the tether through eyelet (436) causes anchor (426) to be slidably engaged with the tether. Thus, if the tether is cinched, then the tether will slide through eyelet (436). Tether (422) can be threaded through multiple anchors in this manner.

As noted above, the method described with reference to FIGS. 4A-4I can be repeated as desired to deploy multiple (e.g., at least two, at least three) anchors that can self-secure to various regions of the mitral valve annulus (AN). As an example, in some variations, five different delivery catheters can be successively advanced over a single tether to deploy five anchors into different regions of the mitral valve annulus. As another example, in certain variations, eight anchors can be deployed into the mitral valve annulus, along an arc of about 240°. Again, the deployed anchors can be uniformly spaced apart, or can have varying amounts of space between them. After multiple anchors have been secured to the region of the mitral valve annulus, tether (422) can be cinched, thereby pulling the anchors closer together, and reducing the circumference of the mitral valve annulus.

Tether (422) can be terminated after the desired extent of reduction has been achieved (e.g., as determined by ultrasound and fluoroscopy). As an example, a clip can be attached to tether (422) proximal to the proximal-most anchor, to maintain the tension of tether (422) between the anchors. Tether (422) can then be cut proximal to the clip. As described in further detail below, in some variations, attachment and cutting can be achieved using a termination device, such as a termination catheter. For example, one or more cutting and/or locking catheters can be used to maintain the tension in a cinched guide element and to remove the unused portion of the guide element, after cinching has been completed. Termination devices are described, for example, in U.S. patent application Ser. Nos. 11/232,190 and 11/270,034, both of which are hereby incorporated by reference in their entirety.

Some methods of terminating tether (422) may include withdrawing tunnel catheter (410) from guide catheter (404) prior to advancing a termination catheter over tether (422) to the proximal-most anchor. The termination catheter may then be used for attachment and cutting of tether (422). Other methods may include first attaching a clip to tether (422) proximal to the proximal-most anchor to maintain the tension in tether (422), and then withdrawing tunnel catheter (410) from guide catheter (404). In certain variations, a method may include attaching tether (422) to the proximal-most secured anchor, and then cutting tether (422) proximal to the anchor to which tether (422) has been attached. Tether (422) can be attached to the proximal-most anchor using, for example, one or more adhesives, and/or one or more knotting, crimping, and/or tying techniques. While threading, cinching, and termination techniques have been described with respect to a tether, these techniques may be used with other guide elements as well.

A guide element can be threaded through a termination catheter in any of a number of different ways. For example, FIGS. 10A-10E show examples of different routings of tethers through locking catheters, and FIGS. 11A-11C show examples of different routings of tethers through cutting catheters.

Figure 10A:
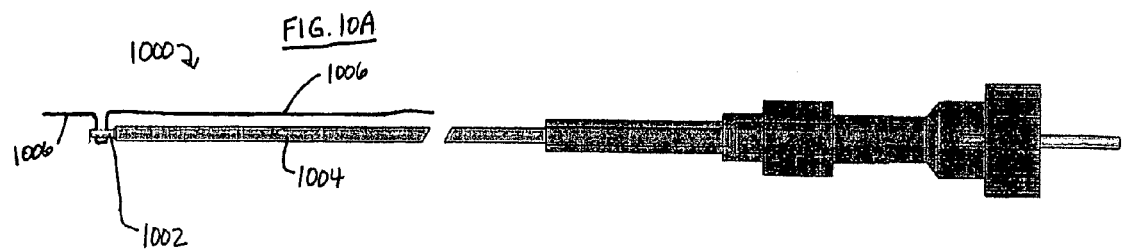
Figure 10B:
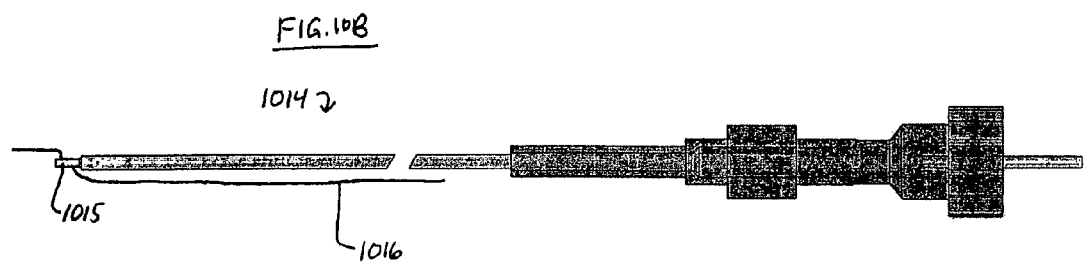
Figure 10C:
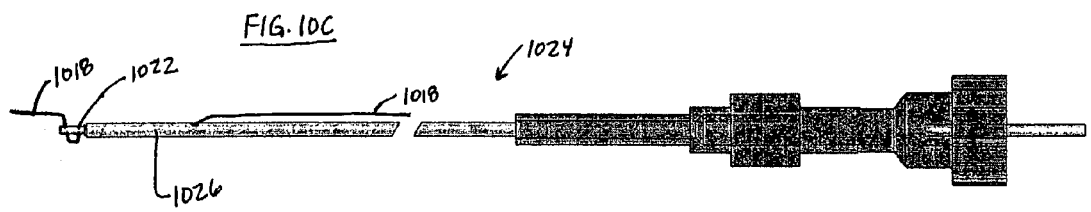
Figure 10D:
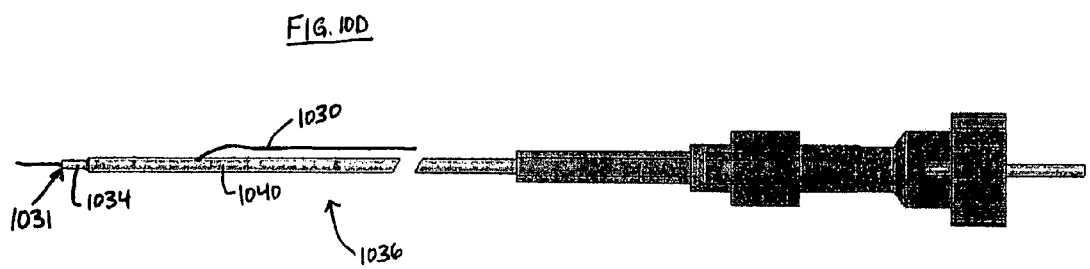

Referring to FIG. 10A, a locking catheter (1000) includes a tip (1002) and a shaft (1004). A tether (1006) is threaded through four openings in the tip, so that the locking catheter secures the tether, thereby maintaining the tension in the tether. While tether (1006) is threaded through four openings in tip (1002), guide elements can be threaded through different numbers of openings in a catheter tip. For example, FIG. 10B shows a locking catheter (1014) including a tip (1015), and a tether (1016) that has been threaded through two openings in the tip of the locking catheter. In FIG. 10C, a tether (1018) is threaded through three openings in a tip (1022) of a locking catheter (1024), and also is threaded into the shaft (1026) of the locking catheter. The tether eventually exits the shaft through an opening in the shaft. FIG. 10D shows a tether (1030) that is threaded into the distal end (1031) of the tip (1034) of a locking catheter (1036), and that extends through the shaft (1040) of the locking catheter, exiting through an opening in the shaft. Guide elements can extend through varying lengths of a shaft of a delivery catheter. For example, while the tether in FIG. 10D extends through a relatively short length of the catheter shaft, FIG. 10E shows a tether that extends through a relatively long length of a catheter shaft. As shown in FIG. 10E, a tether (1042) is threaded into an opening in a tip (1046) of a locking catheter (1048), and extends through almost the entire length of the shaft (I 050) of the locking catheter. Tether (1042) exits the shaft through an opening in the proximal end (I OS 1) of the shaft.

As noted above, guide elements may also be threaded through cutting catheters in different routing configurations. For example, FIG. 11A shows a cutting catheter (1100) including a tip portion (1102) and a shaft portion (1104). A tether (1106) is threaded through two openings in tip portion (1102). A cutting element (1108) is disposed within a lumen of shaft portion (1104), and can be used to cut the tether (e.g., after a cinching procedure has taken place). FIG. 11B shows a different routing configuration for a tether that is threaded through a cutting catheter. As shown in FIG. 11B, a cutting catheter (1110) includes a tip portion (1112) and a shaft portion (1114) containing a cutting element (1118). A tether (1116) is threaded into tip portion (1112) at its distal end (1119), and through three openings in the tip portion. Referring now to FIG. 11C, a cutting catheter (1120) includes a tip portion (1122) and a shaft portion (1124). A tether (1126) is threaded into the tip portion (1122) at its distal end (1127), and exits the tip portion through an opening that is proximal to distal end (1127). A cutting element (1128) is disposed within shaft portion (1124). Guide elements can be threaded through different numbers of holes in cutting catheters and/or through different locations in cutting catheters. All of the described threading variations are merely illustrative examples of suitable threading techniques.

Furthermore, while routing configurations for guide elements through locking catheters and cutting catheters have been shown, the routing configurations may be used in other types of catheters as well. Additionally, other routing configurations may be used to thread a guide element through a catheter. As an example, in some variations, a guide element may not be threaded through a tip of a catheter.

While the methods described herein have been described with respect to anchor deployment, the methods can be used to deploy any number and/or type of suitable implants. For example, an implant may include one or more anchors, may include a lead or electrode (e.g., a pacing electrode, a diagnostic electrode, an active electrode), or may include any other suitable implant. In some variations, an implant may include a fabric implant, or an annuloplasty ring, alone or in combination with one or more anchors. Additional examples of implants include implants that deliver therapy, such as drug-delivery implants, and implants that telemetry information, such as information about the conditions of the target site. For example, implants may be used to deliver growth factors and/or genetic regenerative factors. Implants are described, for example, in U.S. patent application Ser. Nos. 10/461,043, 10/656,797, 10/741,130, 10/776,682, 10/792, 681, 10/901,019, 10/901,555, 10/901,554, 10/901,445, and 10/901,444, all of which are hereby incorporated by reference in their entirety.

While the methods and devices have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the appended claims.

What is claimed is:

1. A method comprising:
   successively advancing a plurality of catheters over a guide element that is attached to a body tissue with an anchor, wherein at least a portion of the guide element remains attached to the body tissue as an implant for treating the body tissue after the catheters have been withdrawn from the body tissue.

2. The method of claim 1, wherein the body tissue is accessible minimally invasively.

3. The method of claim 1, further comprising deploying at least one additional implant from at least one of the plurality of catheters.

4. The method of claim 3, wherein the at least one additional implant is at least one anchor.

5. The method of claim 4, wherein the at least one anchor self-expands and self-secures into a region of the body tissue.

6. The method of claim 3, wherein the at least one additional implant is at least one electrode.

7. The method of claim 1, wherein the body tissue comprises heart tissue.

8. The method of claim 7, wherein the heart tissue comprises mitral valve tissue.

9. The method of claim 1, wherein at least one of the plurality of catheters is a drug delivery catheter.

10. The method of claim 1, wherein at least one of the plurality of catheters is a locking catheter or a cutting catheter.

11. The method of claim 1, wherein the guide element comprises a suture.

12. The method of claim 1, wherein at least one of the plurality of catheters has a proximal section and a distal section, and defines a lumen that is located in the distal section and not in the proximal section.

13. The method of claim 12, wherein the lumen is configured to allow passage of a tether therethrough.

14. A method comprising:
   successively advancing a plurality of catheters over an implant, wherein the implant is attached with an anchor to a body tissue that is accessible minimally invasively and at least a portion of the implant remains attached to the body tissue to treat the body tissue after the plurality of catheters have been withdrawn from the body tissue.

15. The method of claim 14, further comprising deploying at least one additional implant from at least one of the plurality of catheters.

16. The method of claim 15, wherein the at least one additional implant is at least one anchor.

17. The method of claim 16, wherein the at least one anchor self-expands and self-secures into a region of the body tissue.

18. The method of claim 15, wherein the at least one additional implant is at least one electrode.

19. The method of claim 14, wherein the body tissue comprises heart tissue.

20. The method of claim 19, wherein the heart tissue comprises mitral valve tissue.

21. The method of claim 14, wherein at least one of the plurality of catheters is a drug delivery catheter.

22. The method of claim 14, wherein at least one of the plurality of catheters is a locking catheter or a cutting catheter.

23. The method of claim 14, wherein the implant comprises a suture.

24. The method of claim 14, wherein at least one of the plurality of catheters has a proximal section and a distal section, and defines a lumen that is located in the distal section and not in the proximal section.

25. The method of claim 24, wherein the lumen is configured to allow passage of a tether therethrough.

26. A method comprising:
   advancing a first delivery catheter to a first region of a body tissue;
   deploying a first anchor from the first delivery catheter, wherein the first anchor is attached to a guide element;
   proximally withdrawing the first delivery catheter;
   advancing a second delivery catheter over the guide element; and
   deploying a second anchor from the second delivery catheter.

27. The method of claim 26, wherein the guide element comprises a tether.

28. The method of claim 27, wherein the tether comprises a suture.

29. The method of claim 28, wherein the suture comprises polyester impregnated with polytetrafluoroethylene.

30. The method of claim 26, wherein the second anchor is slidably coupled to the guide element.

31. The method of claim 30, wherein the second anchor comprises an eyelet, and the second anchor is slidably coupled to the guide element by engaging the guide element with a lasso and proximally withdrawing the lasso through the eyelet.

32. The method of claim 26, wherein the first and second anchors are deployed to different regions of the body tissue.

33. The method of claim 26, wherein the first and second anchors self-expand and self-secure into different regions of the body tissue.

34. The method of claim 26, wherein advancing the first delivery catheter to the first region of the body tissue comprises advancing the first delivery catheter through a tunnel catheter.

35. The method of claim 34, wherein the tunnel catheter comprises a generally tubular member having an opening.

36. The method of claim 35, wherein the opening is positioned on a side wall of the generally tubular member.

37. The method of claim 35, wherein the generally tubular member has a proximal end and a distal end, and the opening is located proximal to the distal end of the generally tubular member.

38. The method of claim 35, wherein advancing the first delivery catheter through the tunnel catheter comprises advancing a portion of the first delivery catheter through the opening in the wall of the generally tubular member.

39. The method of claim 34, further comprising positioning the tunnel catheter at a second region of the body tissue prior to advancing the second delivery catheter over the guide element.

40. The method of claim 34, wherein the tunnel catheter has a proximal portion and a distal portion, and the distal portion of the tunnel catheter is pre-shaped to include at least one curve.

41. The method of claim 26, wherein the method is used to deploy at least three anchors.

42. The method of claim 26, wherein the body tissue is heart tissue.

43. The method of claim 42, wherein the heart tissue comprises mitral valve tissue, where the mitral valve comprises an annulus.

44. The method of claim 43, further comprising cinching the guide element to reduce the circumference of the mitral valve annulus.

45. The method of claim 43, further comprising cinching the guide element to reduce mitral valve regurgitation.

46. The method of claim 43, further comprising cinching the guide element to effect a geometric change in at least one of the mitral valve annulus and tissue surrounding the mitral valve annulus.

47. The method of claim 43, further comprising cinching the guide element to enhance apposition of leaflets of the mitral valve.

48. The method of claim 26, wherein the second delivery catheter has a first lumen and a second lumen.

49. The method of claim 48, wherein the second anchor is releasably coupled to a suture that is disposed within the second lumen.

50. The method of claim 26, wherein the second delivery catheter has a proximal section and a distal section, and the second delivery catheter defines a lumen that is located in the distal section and not in the proximal section.

51. The method of claim 50, wherein the lumen is configured to allow passage of a tether therethrough.

52. A catheter for advancement along a tether comprising a first and a second lumen, wherein the first and second lumens are positioned adjacent to one another and wherein at least a portion of the first and second lumens is configured to allow the passage of the tether therethrough, and wherein the second lumen is accessible from the first lumen and wherein the second lumen is shorter than the first lumen.

53. The catheter of claim 52, wherein the catheter has a proximal section and a distal section, and the second lumen that is located in the distal section and not in the proximal section.

54. The catheter of claim 52, wherein the catheter is a delivery catheter.

55. The catheter of claim 54, wherein the delivery catheter is configured to deliver at least one anchor and wherein the anchor is positioned in the first lumen.

56. The catheter of claim 52, wherein the catheter is a cutting catheter.

57. The catheter of claim 52, wherein the catheter is a termination catheter.

\* \* \* \* \*